(12) United States Patent
Roussel et al.

(10) Patent No.: US 11,759,677 B2
(45) Date of Patent: Sep. 19, 2023

(54) RESPIRATORY TRAINING AND AIRWAY PRESSURE MONITORING DEVICE

(71) Applicant: UNIVERSITY OF LOUISVILLE RESEARCH FOUNDATION, INC., Louisville, KY (US)

(72) Inventors: Thomas J. Roussel, Louisville, KY (US); Susan J. Harkema, Louisville, KY (US); Alexander V. Ovechkin, Louisville, KY (US); Yangshen Chen, Louisville, KY (US); Kevin Tran, Prospect, KY (US); Edward Hoyt Brown, Jr., Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 394 days.

(21) Appl. No.: 16/969,279

(22) PCT Filed: Feb. 14, 2019

(86) PCT No.: PCT/US2019/018024
§ 371 (c)(1),
(2) Date: Aug. 12, 2020

(87) PCT Pub. No.: WO2019/161065
PCT Pub. Date: Aug. 22, 2019

(65) Prior Publication Data
US 2021/0001169 A1    Jan. 7, 2021

Related U.S. Application Data

(60) Provisional application No. 62/710,395, filed on Feb. 16, 2018.

(51) Int. Cl.
*A63B 23/18* (2006.01)
*A63B 71/06* (2006.01)
(Continued)

(52) U.S. Cl.
CPC .......... *A63B 23/18* (2013.01); *A63B 24/0062* (2013.01); *A63B 71/0622* (2013.01);
(Continued)

(58) Field of Classification Search
CPC . A63B 23/18; A63B 24/0062; A63B 71/0622; A63B 2071/0625;
(Continued)

(56) References Cited

U.S. PATENT DOCUMENTS 3,991,304 A   9/1976 Hillsman
4,011,859 A   3/1977 Frankenberger
(Continued)

FOREIGN PATENT DOCUMENTS

AU   2005318949 B2   6/2006
AU   2007222882 B2   9/2007
(Continued)

OTHER PUBLICATIONS

The European Patent Office, Extended European Search Report, dated Feb. 22, 2021, pp. 1-7, The European Patent Office, Munich, Germany.

(Continued)

*Primary Examiner* — Sundhara M Ganesan
(74) *Attorney, Agent, or Firm* — Wyatt, Tarrant & Combs, LLP; Max E. Bridges; Stephen C. Hall

(57) ABSTRACT

A respiratory training device providing both inspiratory and expiratory functional evaluation and training, as well as independent regulation of both the inspiratory and expiratory airway resistance levels used during training. The respiratory training device also includes data acquisition, recording, storage, retrieval and display functions for airway pressure monitoring data to provide functional evaluation, physiological monitoring, and diagnostic features. The respiratory training device allows the user to easily develop (Continued)

and follow precise and advanced training protocols, and utilize the respiratory device in both the clinical and home setting.

14 Claims, 23 Drawing Sheets

(51) Int. Cl.
    *A61M 16/08*     (2006.01)
    *A61M 16/20*     (2006.01)
    *A61M 16/00*     (2006.01)
    *A63B 24/00*     (2006.01)

(52) U.S. Cl.
    CPC ..... *A61M 16/0833* (2014.02); *A61M 16/0858* (2014.02); *A61M 16/208* (2013.01); *A61M 2016/0027* (2013.01); *A61M 2205/8206* (2013.01); *A63B 2071/0625* (2013.01); *A63B 2071/0675* (2013.01); *A63B 2225/20* (2013.01); *A63B 2225/50* (2013.01); *A63B 2230/40* (2013.01)

(58) Field of Classification Search
    CPC ........ A63B 2071/0675; A63B 2225/20; A63B 2225/50; A63B 2230/40; A63B 24/0087; A63B 24/0075; A63B 71/0686; A63B 2024/0068; A63B 2024/0093; A63B 2071/065; A63B 2071/0694; A63B 2220/56; A63B 2220/62; A63B 2225/74; A63B 2230/42; A61M 16/0833; A61M 16/0858; A61M 16/208; A61M 2016/0027; A61M 2205/8206; A61M 16/0866; A61M 16/024; A61M 16/049; A61M 16/202; A61M 2205/3553; A61M 2205/3592; A61M 2205/505; A61M 2205/52; A61M 2205/583; A61M 2207/00; A61M 2230/42; A61M 16/201; A61B 5/6803; A61B 5/0816; A61B 5/0803; A61B 5/087
    See application file for complete search history.

(56) References Cited

U.S. PATENT DOCUMENTS

| | | | |
|---|---|---|---|
| 4,241,739 A | 12/1980 | Elson | |
| 4,533,137 A | 8/1985 | Sonne | |
| 4,739,987 A | 4/1988 | Nicholson | |
| 4,984,158 A | 1/1991 | Hillsman | |
| 5,067,707 A | 11/1991 | Kohnke | |
| 5,255,687 A | 10/1993 | McKenna | |
| 5,357,975 A | 10/1994 | Kraemer et al. | |
| 6,066,101 A | 5/2000 | Johnson et al. | |
| 6,631,716 B1 | 10/2003 | Robinson et al. | |
| 6,942,625 B1 | 9/2005 | Bryant | |
| 8,459,255 B2 | 6/2013 | Spurling et al. | |
| 8,539,951 B1 | 9/2013 | Meyer et al. | |
| 9,002,427 B2 | 4/2015 | Tupin, Jr. et al. | |
| 9,452,317 B2 | 9/2016 | Arkush | |
| 2002/0123692 A1 | 9/2002 | Pail | |
| 2003/0065272 A1 | 4/2003 | Hillsman | |
| 2004/0267086 A1 | 12/2004 | Anstadt et al. | |
| 2005/0284476 A1 | 12/2005 | Blanch et al. | |
| 2007/0107728 A1 | 5/2007 | Ricciardelli et al. | |
| 2007/0122785 A1 | 5/2007 | Eggert et al. | |
| 2007/0221225 A1 | 9/2007 | Kutt et al. | |
| 2008/0138779 A1 | 6/2008 | Eggert et al. | |
| 2008/0138780 A1 | 6/2008 | Eggert et al. | |
| 2009/0229611 A1 | 9/2009 | Martin et al. | |
| 2009/0264255 A1 | 10/2009 | Tutsch et al. | |
| 2009/0270751 A1 | 10/2009 | Peng et al. | |
| 2010/0078015 A1 | 4/2010 | Imran | |
| 2011/0060215 A1 | 3/2011 | Tupin, Jr. et al. | |
| 2011/0073107 A1 | 3/2011 | Rodman et al. | |
| 2012/0041329 A1 | 2/2012 | Chatam | |
| 2012/0272956 A1* | 11/2012 | Rusher ................ A61M 16/209 |
| | | | 128/205.24 |
| 2014/0276100 A1 | 9/2014 | Satterfield et al. | |
| 2014/0276173 A1 | 9/2014 | Banner et al. | |
| 2015/0011906 A1 | 1/2015 | Wallach | |
| 2015/0087948 A1 | 3/2015 | Bishay et al. | |
| 2015/0120067 A1 | 4/2015 | Wing et al. | |
| 2015/0154888 A1 | 6/2015 | Eggert et al. | |
| 2015/0283337 A1 | 10/2015 | Adams et al. | |
| 2015/0283341 A1 | 10/2015 | Adams et al. | |
| 2016/0120462 A1 | 5/2016 | Tunnell et al. | |
| 2016/0372009 A1 | 12/2016 | Eggert et al. | |
| 2017/0000382 A1 | 1/2017 | Leydon | |
| 2017/0020439 A1 | 1/2017 | Chatham et al. | |
| 2017/0259019 A1 | 9/2017 | Cariola et al. | |
| 2017/0279830 A1 | 9/2017 | Mermound et al. | |
| 2018/0092595 A1 | 4/2018 | Chen et al. | |
| 2018/0243608 A1 | 8/2018 | Jones et al. | |
| 2019/0290959 A1* | 9/2019 | Chesbrough ......... A61B 5/4836 |

FOREIGN PATENT DOCUMENTS

| | | |
|---|---|---|
| AU | 2008316556 B2 | 4/2009 |
| AU | 2009259883 B2 | 12/2009 |
| CA | 2379188 A1 | 2/2001 |
| CA | 2381817 A1 | 3/2001 |
| CA | 2398949 A1 | 8/2001 |
| CA | 2645643 A1 | 11/2006 |
| CA | 2661152 A1 | 2/2008 |
| CA | 2755859 A1 | 9/2010 |
| CA | 2766064 A1 | 12/2010 |
| CA | 2463088 C | 3/2012 |
| CA | 2808836 C | 3/2012 |
| CA | 2824971 A1 | 7/2012 |
| CA | 2867745 A1 | 9/2013 |
| CA | 2494819 C | 11/2013 |
| CA | 2883445 A1 | 3/2014 |
| CA | 2897883 A1 | 7/2014 |
| CA | 2922981 A1 | 4/2015 |
| CA | 2716511 C | 6/2015 |
| CA | 2969460 A1 | 6/2016 |
| CA | 2994792 A1 | 2/2017 |
| CA | 2995289 A1 | 2/2017 |
| CA | 2805124 C | 11/2017 |
| CA | 3018631 A1 | 11/2017 |
| CA | 2859925 C | 2/2019 |
| CA | 3022916 C | 3/2020 |
| CN | 2090274 U | 12/1991 |
| CN | 100998902 A | 7/2007 |
| CN | 200960375 A | 10/2007 |
| CN | 101822894 A | 9/2010 |
| CN | 102151385 A | 8/2011 |
| CN | 102764492 A | 11/2012 |
| CN | 202802661 A | 3/2013 |
| CN | 103341254 A | 10/2013 |
| CN | 203329293 A | 12/2013 |
| CN | 103736256 A | 4/2014 |
| CN | 203677868 Y | 7/2014 |
| CN | 104042439 A | 9/2014 |
| CN | 203915949 U | 11/2014 |
| CN | 204352476 U | 5/2015 |
| CN | 104799820 A | 7/2015 |
| CN | 104939815 A | 9/2015 |
| CN | 105381570 A | 3/2016 |
| CN | 205127309 U | 4/2016 |
| CN | 105561451 A | 5/2016 |
| CN | 105688372 A | 6/2016 |
| CN | 105879329 A | 8/2016 |
| CN | 106137202 A | 11/2016 |
| CN | 106236097 A | 12/2016 |
| CN | 106308839 A | 1/2017 |
| CN | 106581948 A | 4/2017 |
| CN | 106669110 A | 5/2017 |
| CN | 106807039 A | 6/2017 |
| CN | 107320913 A | 11/2017 |

(56) References Cited

FOREIGN PATENT DOCUMENTS

| | | |
|---|---|---|
| CN | 107802993 A | 3/2018 |
| CN | 107899201 A | 4/2018 |
| DE | 3827636 A1 | 2/1989 |
| DE | 102008028662 A1 | 12/2008 |
| DE | 102007039124 A1 | 2/2009 |
| DE | 102010036625 A1 | 1/2012 |
| DE | 102012200815 B3 | 1/2013 |
| DE | 102013001913 A1 | 8/2014 |
| DE | 102015015296 A1 | 6/2017 |
| DE | 102009041425 A1 | 8/2017 |
| EP | 0520082 A1 | 12/1992 |
| EP | 0667168 A1 | 8/1995 |
| EP | 0756850 B1 | 9/1995 |
| EP | 0984828 B1 | 3/1998 |
| EP | 1025799 A1 | 8/2000 |
| EP | 2022541 A1 | 2/2009 |
| EP | 2111790 A1 | 10/2009 |
| EP | 2407102 A1 | 1/2012 |
| EP | 2489413 | 8/2012 |
| EP | 2708260 A1 | 3/2014 |
| EP | 3097936 A1 | 11/2016 |
| ES | 071528 U | 3/2010 |
| FR | 2345130 A1 | 10/1977 |
| GB | 2278545 A | 6/1993 |
| JP | 08164225 A | 6/1996 |
| JP | 2011197128 A | 10/2011 |
| JP | 2016179187 A | 10/2016 |
| KR | 20180073839 A | 7/2018 |
| TW | 200938110 A | 9/2009 |
| WO | 9215353 A2 | 9/1992 |
| WO | 02081034 A2 | 10/2002 |
| WO | 2004073516 A1 | 9/2004 |
| WO | 2005123165 A1 | 12/2005 |
| WO | 2007079068 A2 | 7/2007 |
| WO | 2007083495 A1 | 7/2007 |
| WO | 2007103396 A2 | 9/2007 |
| WO | 2008122806 A1 | 10/2008 |
| WO | 2011004274 A1 | 1/2011 |
| WO | 2011019091 A1 | 2/2011 |
| WO | 2011048244 A1 | 4/2011 |
| WO | WO-2011048244 A1 * | 4/2011 ............ A61B 5/087 |
| WO | 2012020433 A1 | 2/2012 |
| WO | 2012030645 A1 | 3/2012 |
| WO | 2012037641 A1 | 3/2012 |
| WO | 2013152403 A1 | 10/2013 |
| WO | 2013177621 A1 | 12/2013 |
| WO | 2013179181 A1 | 12/2013 |
| WO | 2014045221 A1 | 3/2014 |
| WO | 2014053242 A1 | 4/2014 |
| WO | 2014059389 A1 | 4/2014 |
| WO | 2014097055 A1 | 6/2014 |
| WO | 2015066562 A2 | 5/2015 |
| WO | 2015120435 A1 | 8/2015 |
| WO | 2015120521 A1 | 8/2015 |
| WO | 2015120522 A1 | 8/2015 |
| WO | 2015179911 A1 | 12/2015 |
| WO | 2015200900 A1 | 12/2015 |
| WO | 2016019292 A1 | 2/2016 |
| WO | 2016029265 A1 | 3/2016 |
| WO | 2016074042 A1 | 5/2016 |
| WO | 2016116591 A1 | 7/2016 |
| WO | 2016145483 A1 | 9/2016 |
| WO | 2017006189 A1 | 1/2017 |
| WO | 2017071879 A1 | 5/2017 |
| WO | 2017071964 A1 | 5/2017 |
| WO | 2017072036 A1 | 5/2017 |
| WO | 2017132726 A1 | 8/2017 |
| WO | 2017136336 A1 | 8/2017 |
| WO | 2017167630 A1 | 10/2017 |
| WO | 2017178776 A1 | 10/2017 |
| WO | 2017201463 A1 | 11/2017 |
| WO | 2018011358 A1 | 1/2018 |
| WO | 2018085563 A1 | 5/2018 |

OTHER PUBLICATIONS

The United States Patent and Trademark Office, The International Search Report and The Written Opinion of the International Searching Authority, or the Declaration, dated May 13, 2019, pp. 1-16, The United States Patent and Trademark Office, USA.

Carefusion Corporation, Copyright 2012, AirLife Respiratory Products, Product Catalog, p. 1-3, 45-46, 176; carefusion.com/AirLife2012 http://site.aaawholesalecompany.com/Files/Carefusion-Airlife.pdf.

Philips Respironics, Copyright 2010 Product Catalog; Mar. 20, 2013 Koninklijke Philips Electronics N.V., Product Catalog, pp. 1-3, 92, 148; www.philips.com/respironics. https://cdnmedia.endeavorsuite.com/images/organizations/761cd3db-bc93-4b30-a408-1a16cfec1521/Migration/manuals%20and%20pdf/24.pdf.

Gea, Joaquim, et al, Respiratory diseases and muscle dysfunction. Expert Review of Respiratory Medicine. Feb. 2012; 6(1), 75-90 (2012).

Daniela G. L. Terson de Paleville, et al. "Respiratory Motor Control Disrupted by Spinal Cord Injury: Mechanisms, Evaluation, and Restoration." Manuscript. Translational stroke research. U.S. National Library of Medicine, Dec. 1, 2011, 2(4):463-473; www.ncbi.nlm.nih.gov/pmc/articles/PMC3297359/.

Ovechkin, Alexander V., et al. "Respiratory motor training and neuromuscular plasticity in patients with chronic obstructive pulmonary disease: a pilot study." Manuscript. Respiratory physiology & neurobiology, U.S. National Library of Medicine, Jul. 15, 2016, 229: 59-64. doi:10.1016/j.resp.2016.04.003; www.ncbi.nlm.nih.gov/pmc/articles/PMC4887410/.

"Micro Diary Spirometer." MedicalDeviceDepot.com; Copyright 2020, accessed Dec. 2017, Medical Device Depot, Inc.; Product brochure, http://www.meddevicedepot.com/PDFs/MicroDiaryBrochure.pdf.

MGC Diagnostics: Ultima PF™ pulmonary function system with RTD. Copyright 2012-2020, accessed Dec. 2017 MGC Diagnostics Corporation. Product brochure, https://mgcdiagnostics.com/images/products/Ultima_PF_Standalone_sellsheet_web.pdf.

"Overcome the Pressure for Consistent PEP and IMT Therapy." Respironics, Respironics, Product catalog, http://www.dolema.com/wp-content/uploads/2017/07/1036501_4_ThresholdSht_5.pdf.

"PendoTech PRESS-S-000 PressureMAT Single-Use Sensor, Luer Fitting, Polycarbonate." Cole-Parmer, www.coleparmer.com, Copyright 2020, accessed Dec. 2017. Cole-Parmer Instrument Company, LLC. Product catalog, p. 574; https://www.coleparmer.com/virtual-catalog/gh3/574.

Industries, Adafruit. "Adafruit Assembled Data Logging shield for Arduino." Copyright 2020, accessed in 2017. Adafruit industries blog RSS, Product catalog, www.adafruit.com/product/1141#technical-details.

"ULCD-32PTU." 4D Systems, Copyright 2020, accessed in 2017. Product catalog, www.4dsystems.com.au/product/uLCD_32PTU/.

Arduino, "Compare Board Specs." Copyright 2020, accessed in 2017. Product catalog, https://www.arduino.cc/en/Products/Compare.

"Powerbreathe Kinetic K5 Breathing Trainer". Copyright 2020, accessed in 2017. POWERbreathe International Limited. Product catalog, https://www.powerbreathe.com/powerbreathe-k5.

Schilero, et al Traumatic Spinal Cord Injury: Pulmonary Physiologic Principles and Management. Clin Chest Med 39 (2018) 411-425; https://doi.org/10.1016/j.ccm.2018.02.002; 0272-5231/18/ Published by Elsevier Inc.

Linn, et al Pulmonary Function in Chronic Spinal Cord Injury: A Cross-Sectional Survey of 222 Southern California Adult Outpatients; Arch Phys Med Rehabil, Jun. 2000; 81 pp. 757-763.

Laffont, et al. Breathlessness Associated With Abdominal Spastic Contraction in a pPatient With C4 Tetraplegia: A Case Report. Arch Phys Med Rehabil., Jun. 2003; 84(6): pp. 906-908.

Crisafulli, et al. Respiratory muscles training in COPD patients; International Journal of COPD 2007:2(1) pp. 19-25.

Jolley, et al. Neural respiratory drive in healthy subjects and in COPD; European Respiratory Journal, 2009:33, pp. 289-297.

(56) References Cited

OTHER PUBLICATIONS

McKenzie, et al. Respiratory muscle function and activation in chronic obstructive pulmonary disease J. Appl. Physiol., 107 (2009), pp. 621-629; First published Apr. 23, 2009; doi:10.1152/japplphysiol.00163.2009.
Respironics, Copyright 2006 Product Brochure; www.respironics.com; "Oversome the Pressure for Consistent PEP and IMT Therapy." http://www.dolema.com/wp-content/uploads/2017/07/1036501_4_ThresholdSht_5.pdf.
Roussel, et al. "BreathForce: A Portable Respiratory Muscle Training System for Patients with Spinal Cord Injuries" PowerPoint Presentation; Nov. 9, 2017.

* cited by examiner

RESPIRATORY TRAINING AND AIRWAY PRESSURE MONITORING DEVICE

CROSS REFERENCE TO RELATED U.S. APPLICATION

This international nonprovisional patent application claims priority to and benefit from U.S. Provisional Patent Application Ser. No. 62/710,395, titled "Respiratory Training and Airway Pressure Monitoring Device," filed on 16 Feb. 2018, which is hereby incorporated by reference in its entirety.

FIELD OF INVENTION

The embodiments described herein relate to respiratory training and testing devices, sometimes referred to as respiratory devices, which are for functional evaluation, training and quantifying a user's respiratory and cardiovascular fitness and for those wanting or needing to improve their respiratory-cardiovascular performance. The respiratory devices of the present embodiments provide respiratory function measurements, reciprocal inspiratory and expiratory training, as well as independent regulation of both the inspiratory and expiratory resistance levels to be set during training sessions. Further embodiments provide for data acquisition, recording, storage, retrieval and display functions for airway pressure monitoring data to provide functional evaluation, visible feedback for users, progress monitoring, and diagnostic features.

BACKGROUND

A number of underlying physical conditions exist in which pulmonary and cardiovascular dysfunction are manifest in an individual. An abbreviated list of such conditions include spinal cord injury, neurological disorders, chronic obstructive pulmonary disease (COPD), cardiopulmonary and/or cardiovascular disease, stroke, and sleep apnea. In the United States, pulmonary and cardiovascular dysfunction is consistently reported as a leading cause of morbidity and mortality among over 1.2 million people with chronic effects of spinal cord injury. By 2020, it is projected that these types of pulmonary and cardiovascular dysfunctions will be ranked first in terms of the burden of disease created by these conditions.

In this regard, "expiratory" refers to breathing out, or exhaling, and "inspiratory" refers to breathing in, or inhaling. Currently, respiratory muscle training devices and techniques using either inspiratory or expiratory trainers have been used in a rehabilitative approach to improve pulmonary function in some patients with respiratory, pulmonary, and/or cardiovascular deficits or who suffer from the aforementioned chronic diseases. Current respiratory muscle training devices and techniques have also been used to provide respiratory training for athletes to improve respiratory performance and cardiovascular function, for professionals who need to improve vocal function (such as singers, actors), or for any individual that desires to improve their respiratory capacity. Herein, the terms "user" and "patient" are used interchangeably to describe an individual that desires to improve their respiratory capacity.

In therapy or training sessions, users challenge their lungs and keep the muscles that control the lungs active to prevent atrophy, to increase total lung capacity, to increase peak oxygen consumption, or some combination of these and other desired results. In short, it is known that respiratory muscle training/therapy efforts can enhance breathing performance and improve health.

However, a number of conventional respiratory training devices are typically directed to either inspiratory training or expiratory training, but not both. However, if a user desires to train for both inspiration and expiration breathing, they must remove their mouthpiece and switch the mode in between therapy devices for inhalation and exhalation or change devices completely (for devices that are only one way). But in doing so, an inefficiency is created because inspiration and expiration are inextricably linked. In many patients, it is not just a problem of insufficient airflow to the lungs, but also of insufficient ventilation, such that two separate conditioning devices would then be needed for an adequate training program that exercises both inspiratory and expiratory breathing. See e.g. Gea, J. et al., Respiratory diseases and muscle dysfunction. Expert Rev Respir Med. 2012 February; 6(1):75-90. doi: 10.1586/ers.11.81; Ovechkin, A. et al., Respiratory motor training and neuromuscular plasticity in patients with chronic obstructive pulmonary disease: A pilot study. Respir Physiol Neurobiol. 2016; 229:59-64. doi: 10.1016/j.resp.2016.04.003. PubMed PMID: 27137413; PMCID: PMC4887410.

Conventional respiratory training devices present a number of other disadvantages, such as the inability to independently regulate the resistance level of both inspiration and expiration. This shortcoming presents a particular problem to users that desire to develop and implement a training regimen. If users cannot independently regulate the resistance level of both the expiratory and inspiratory levels, then they cannot establish threshold training values and cannot adjust these levels as their training progresses making it much more difficult to improve their respiratory strength. Accordingly, conventional respiratory training devices fail to offer a good balance of functional evaluation, progress monitoring, diagnostic features for training purposes, nor do they develop precise and advanced training patterns for users.

Typically, the conventional respiratory training device consists of either small, personal devices or multi-featured training devices designed for the clinical setting. However, regardless of the setting, these conventional respiratory training devices present a number of other disadvantages. For example, the typical hand-held, personal devices that may be taken home by a user focus only on training and are designed to specifically target and activate respiratory muscles. Typically, these conventional personal devices can only provide measurement of a user's expiratory capacity during one steady deep exhale. For user feedback during an exhalation, users typically see a ball or indicator rise and fall during a full exhale. However, these conventional devices do not show the full capacity of the lungs, are limited to solely expiratory measurements, and fail to quantify inspiratory capacities. Furthermore, the measurements during exhalation are often recorded manually. As a result, these conventional portable devices are typically rudimentary, provide limited functionality, and provide limited accuracy for the user.

In clinical settings, the conventional respiratory training devices are more advanced and provide more features, but these conventional devices are quite bulky, expensive (i.e. ranging in price from $800 to $32,000), and lack many important features such as the independent regulation of the inspiration and expiration resistance levels. In addition, these clinics may be a long distance from the patient and there may be significant gaps between visits to the clinic which make it difficult to implement a training regimen. Due to their size and significant price, these bulky clinical devices are simply not suitable for a user that desires to improve their respiratory performance away from the clinic environment.

In respiratory devices, it is often desirable to utilize a valve in which to control the air flow. However, the commercial electronic proportional valves often utilize small flow paths (e.g. ⅛ of an inch diameter) that can only function in environments with high pressure (such as 100 pounds per square inch ("psi")) and high flow rates. Thus, the conventional electronic proportional valves are not suitable for use in a respiratory training device because they create too much resistance, particularly for a user with compromised pulmonary function.

Accordingly, there is a significant need for a respiratory training device that provides both expiratory and inspiratory muscle training with adjustable independent regulation of inspiration and expiration. Such an improvement would eliminate the need for two separate breathing devices and would facilitate the development and implementation of training regimens. Likewise, there is a need to continuously monitor and record airway pressure monitoring data during training to provide for evaluation, progress monitoring, provide diagnostic features, and develop advanced training sessions. There is a significant need for closed loop control of the training device's adjustable valves to separately regulate the inspiration and expiration threshold levels. Such a feature would allow the user and/or physician to develop and implement advanced training regimens. There is also a need for a portable and affordable device that may be used in both a clinical and home setting. Along with other features and advantages outlined herein, respiratory training devices within the scope of present embodiments meet these and other needs. In doing so, the respiratory training devices within the scope of present embodiments develop advanced training regimens for users, inform users about their training progress over time, and operate in low pressure and low flow rate environments.

SUMMARY OF EMBODIMENTS

Respiratory training devices according to multiple embodiments and alternatives provide both inspiratory and expiratory muscle training, as well as independent regulation of both the inspiratory and expiratory airway resistance levels. The respiratory training device also includes data acquisition, recording, storage, retrieval and display functions for airway pressure monitoring data to provide functional evaluation, progress monitoring, and diagnostic features. An exemplary (i.e., non-limiting) respiratory training device in accordance with present embodiments also provides features that allow the user to develop precise and advanced training protocols, and utilize the respiratory device in both the clinical and home setting.

Current embodiments provide for a respiratory training device that comprises a bi-directional breathing apparatus (i.e. both inspiratory and expiratory), a pressure sensor, and a processing unit configured to record, store, retrieve and display the airway pressure monitoring data and to control the various functions of the training device. In some embodiments, the processing unit is connected to a touchscreen display to generate training programs based on functional measurements, to guide the user through the various training sessions, display the results of the training, and provide visual output from the therapy session to the user. In other embodiments, the breathing apparatus, pressure sensor, and processing unit are a standalone device that is battery-powered or plugged into an outlet, with communication capabilities that wirelessly connect to remote device such as a mobile phone or tablet with an app. The instant (or scheduled) transmission of the respiratory data to a display or mobile app allows a clinician to provide feedback and encouragement to the patient, and allows the clinician to adjust the user's training program as needed. In addition, the transmission of the respiratory training data informs the physician of the patient's progress and motivates the patient to comply with their training regimen when performed outside of the clinic.

In some embodiments, the bi-directional breathing apparatus consists of a mouthpiece that can be flanged and disposable, a connector with two one-way valves, a pressure port to expose the pressure to a pressure sensor, an inspiratory trainer device, and an expiratory training tube. In some embodiments, the one-way valves in the connector open and close with each other such that air can only go through the inspiratory trainer device or out the expiratory training tube, but not both. In other words, when the user inhales, air passes only through the one-way valves of the inspiratory trainer device, through the connector, and through the mouthpiece. When the user exhales through the mouthpiece, the one-way valves in the connector block air from going through the inspiratory trainer device, and instead the air travels through the other one-way valves of the connector and out the expiratory training tube. Current embodiments also provide for manual independent airway resistance adjustment in both the inspiratory trainer and the expiratory training tubes. In some embodiments, the user adjusts the air resistance by manual manipulation of compression springs inside the airway valves. In other embodiments, the processing unit includes a valve controller that electromechanically controls an adjustable valve and the user manually adjusts the valve controller by manually entering the desired airway resistance level into the processing unit. Accordingly, these embodiments provide for both expiratory and inspiratory muscle training with adjustable independent regulation of inspiration and expiration. These embodiments allow a clinician or user to develop precise and advanced training sessions.

In some embodiments, a pressure sensor is connected to the pressure port of the connector. During operation, the pressure sensor detects and measures the air pressure generated when the user both inhales and exhales through the bi-directional breathing apparatus. As previously noted, in some embodiments the pressure sensor is connected to a processing unit, and in other embodiments the sensor is wirelessly connected to a remote device. Regardless, the respiratory training device according to present embodiments includes a data recording function to save and display the airway pressure monitoring data generated during the training session. Furthermore, in some embodiments the processing unit or the remote device (utilizing a mobile app in a non-limiting example) can guide the user through a training session, to display prompts guiding a user through a training session, receive user input, display live air pressure data during a training session, and display the results such that the user can monitor their progress. Accordingly, these embodiments provide for functional evaluation and progress monitoring of the user's training, and provide diagnostic features for training purposes.

In some embodiments, the specific parts that are used in manufacturing a respiratory training device can be obtained as "off the shelf," disposable, sterilized and biocompatible components. In addition, the respiratory training device in current embodiments is small and lightweight. These embodiments ensure that the respiratory training device is affordable, can be easily repaired using interchangeable parts, may be utilized by the user at home or in a clinical setting, and satisfies the United States Pharmacopoeia Class VI requirements established to safeguard the quality of health care technologies. Furthermore, current embodiments provide for a respiratory training device with a large flow path (e.g. 1 inch diameter) that is suitable for the lower pressure training situations that typically arise in therapy sessions.

BRIEF DESCRIPTION OF THE FIGURES

The drawings and embodiments described herein are illustrative of multiple alternative structures, aspects, and features of the present embodiments, and they are not to be understood as limiting the scope of present embodiments. It will be further understood that the drawing figures described and provided herein are not to scale, and that the embodiments are not limited to the precise arrangements and instrumentalities shown.

MULTIPLE EMBODIMENTS AND ALTERNATIVES

Figure 1:
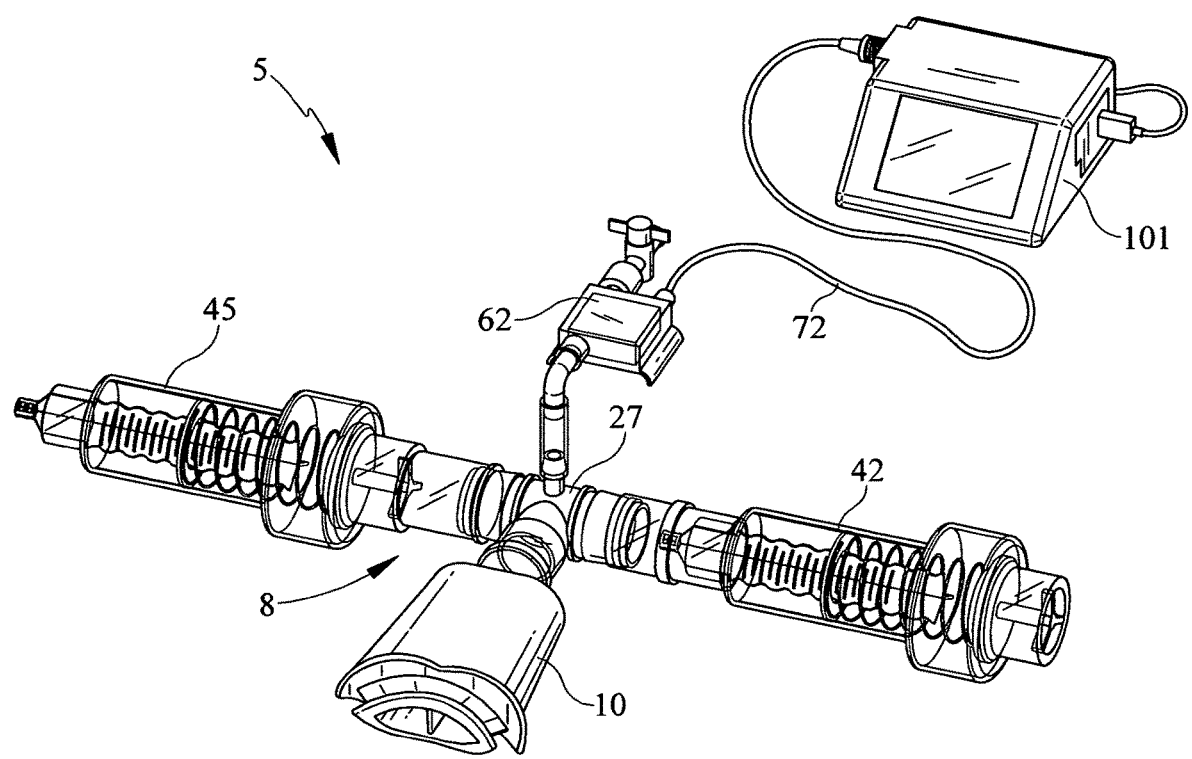
FIG. 1 is a perspective view of a respiratory training device, according to multiple embodiments and alternatives.

In some embodiments, a respiratory training device (sometimes referred to herein as a respiratory device for training a user's respiratory fitness), comprises a bi-directional airflow assembly 8. In some embodiments, the bi-directional airflow assembly 8 comprises an inspiratory training tube 42, an expiratory training tube 45, a connector 27, and a mouthpiece 10, each having a hollow portion. As desired, these parts for the bi-directional airflow assembly 8 are detachable. In some embodiments, the connector is joined directly to the other three parts listed above or, alternatively, joinder is established by adapters that preserve one or more flow paths described herein and defined by the hollow portions of these parts.

In some embodiments, each of the inspiratory training tube 42 and expiratory training tube 45 comprises a valve 60 that lets air flow into the tube when a user inhales through the mouthpiece, or valve 60 lets air flow out of the tube when a user exhales into the mouthpiece. Accordingly, the inspiratory training tube, connector, and mouthpiece define one flow path for air drawn into the bi-directional airflow assembly 8, while the expiratory training tube, connector, and mouthpiece define a different, second flow path for air blown out of the bi-directional airflow assembly 8. Further, a respiratory training device 5 according to multiple embodiments and alternatives comprises a pressure sensor 62 in communication with a first volume of the bi-directional airflow assembly 8 representing a first flow path and a second volume representing a second flow path, in order to obtain an air pressure data within such volumes of the bi-directional airflow assembly 8. Said air pressure data will generally be associated with the user inhaling through, or exhaling into, the mouthpiece during use of device 5. In some embodiments, the air pressure data consists of the inhale pressure, the exhale pressure, the date, the time, and the length of the training session.

FIG. 1 shows respiratory training device 5 according to multiple embodiments and alternatives. Respiratory training device 5 includes mouthpiece 10, connector 27, inspiratory training tube 42, expiratory training tube 45 and pressure sensor 62. In some embodiments, connector 27 is a tee connector. In some embodiments, respiratory training device 5 is connected to a processing unit 101 by a pressure sensor wire 72. In other embodiments, the respiratory training device 5 is a stand-alone unit powered by a battery or plugged into an outlet and wirelessly connected to a remote device (e.g. a phone, tablet, or other device). As a non-limiting example, a stand-alone respiratory training device 5 could be connected to a separate device via Bluetooth® technology.

Figure 2:
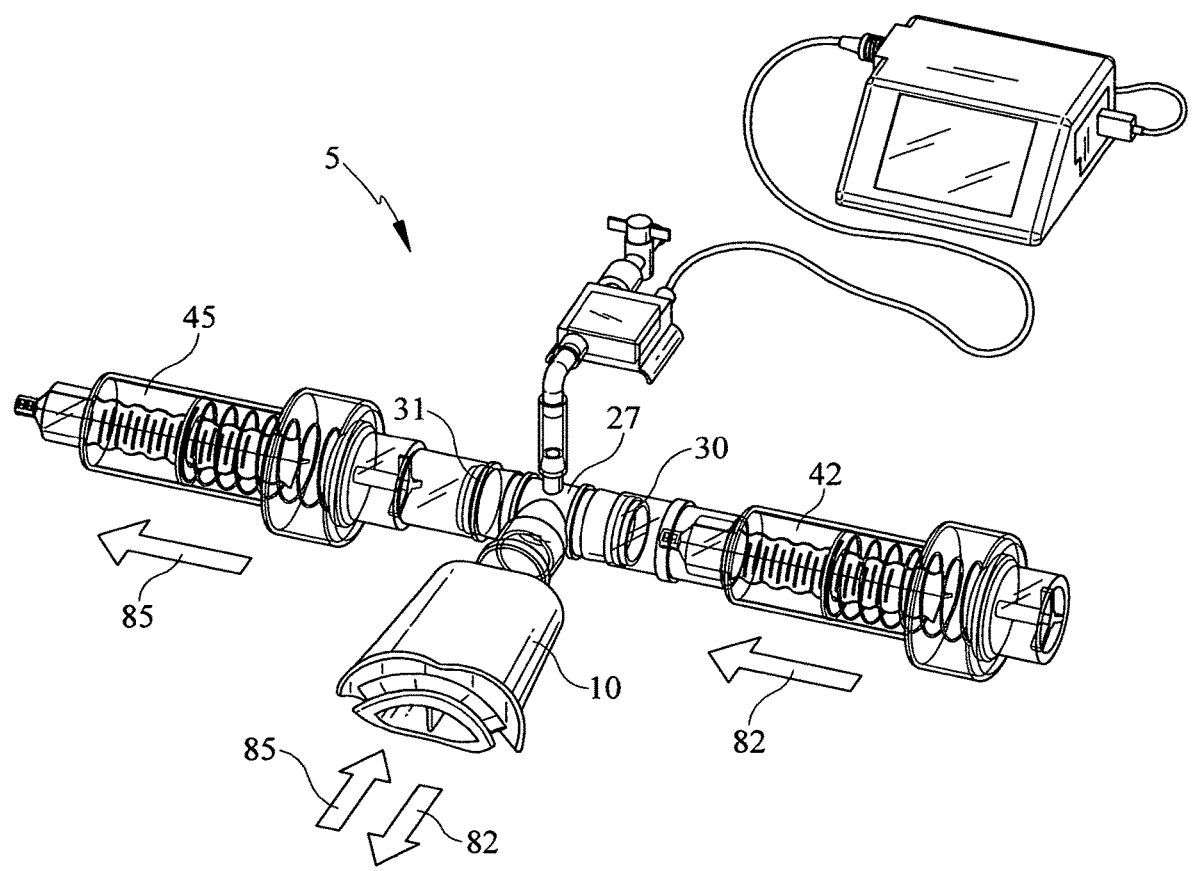
FIG. 2 is a perspective view illustrating the air flow paths through a respiratory training, according to multiple embodiments and alternatives.

In FIG. 2, the arrows 82 illustrate the air flow path when a user inhales through the respiratory training device 5, referred to herein as a first flow path, and arrows 85 illustrate the air flow path when a user exhales, referred to herein as a second flow path. In some embodiments, connector 27 includes one-way valve 30 and one-way valve 31, wherein one-way valve 30 is located near the inspiratory training tube port 38, and one-way valve 31 is near the expiratory training tube port 35. In some embodiments, one-way valve 30 and one-way valve 31 in the connector 27 open and close with each other such that air can only go through the inspiratory trainer device 42 or out the expiratory training tube 45, but not both. In other words, when the user inhales through the respiratory training device 5, air passes along the path shown by arrows 82 through the inspiratory training tube 42, through the connector 27, and through the mouthpiece 10. When the user exhales through the mouthpiece 10, one-way valve 30 and one-way valve 31 in the connector 27 block air from going through the inspiratory training tube 42, and instead the air travels along the path shown by arrows 85 through the other one-way valve of the connector and out the expiratory training tube 45. In some embodiments, either of the valves 30 or 31 could be provided as a single valve that is bi-directional to permit airflow bi-directionally. In this way, in some embodiments a bi-directional valve is used that is within or adjacent to connector 27 that is adjustably configured (e.g., by rotatably) to close the second flow path when air moves along the first flow path, and to close the first flow path when air moves along the second flow path.

Figure 3:
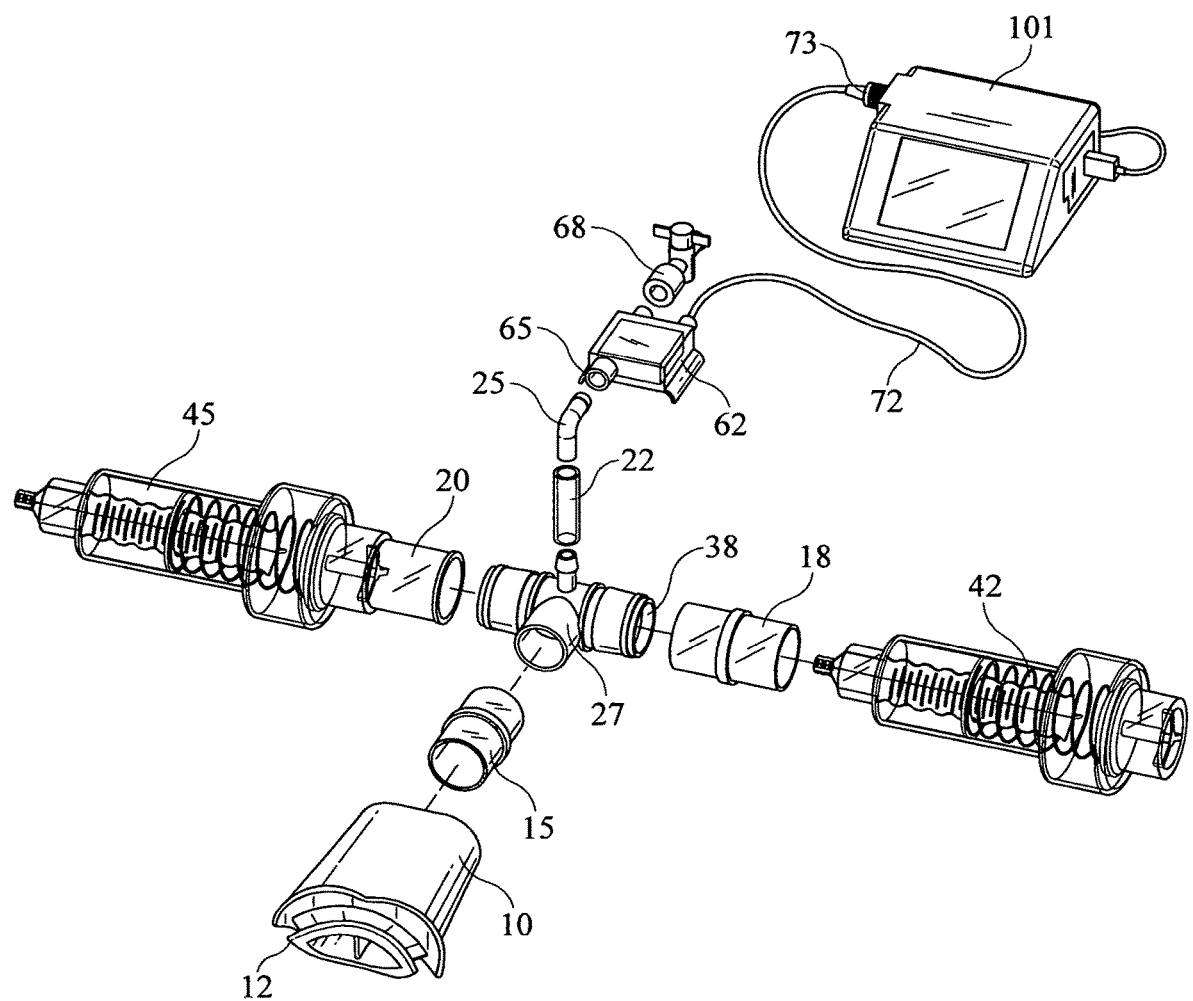
FIG. 3 is an exploded view of a respiratory training device, according to multiple embodiments and alternatives.

FIG. 3 illustrates an exploded view of respiratory training device 5. As shown in FIG. 3, mouthpiece 10 includes a mouthpiece flange 12 to receive the mouth of a user. Mouthpiece 10 connects to mouthpiece adapter 15, which connects to connector 27 via mouthpiece port 40. In some embodiments, the inspiratory training tube 42 and the expiratory training tube 45 are identical (and interchangeable) devices that permit the passage of air flow in one direction. In other embodiments, inspiratory training tube 42 and expiratory training tube 45 are different because the range of inhale and exhale pressures are different, as well as the respective pressure markings on the devices. When a training device is connected to the inspiratory training tube adapter 18, which in turn connects to the connector 27 via inspiratory training tube port 38, the training device only permits air flow into the respiratory training device 5 along path 82. When a training device is connected to the expiratory training tube adapter 20, which in turn connects to the connector 27 via expiratory training tube port 35 (best illustrated in FIG. 6), the training device only permits air flow out the respiratory training device along path 85. Adapters (15, 18, and 20) are optional features and provided in FIG. 3 for illustrative (and non-limiting) purposes. Accordingly, a training device can be used for either inspiration or expiration, and its function will depend on whether the training device is connected to the inspiratory or expiratory side of connector 27. In some embodiments, the inspiratory training tube 42 can only be used for inspiration and the expiratory training tube 45 can only be used for expiration because of the unique inhale and exhale pressures and the unique pressure markings on the respective tubes.

Figure 8:
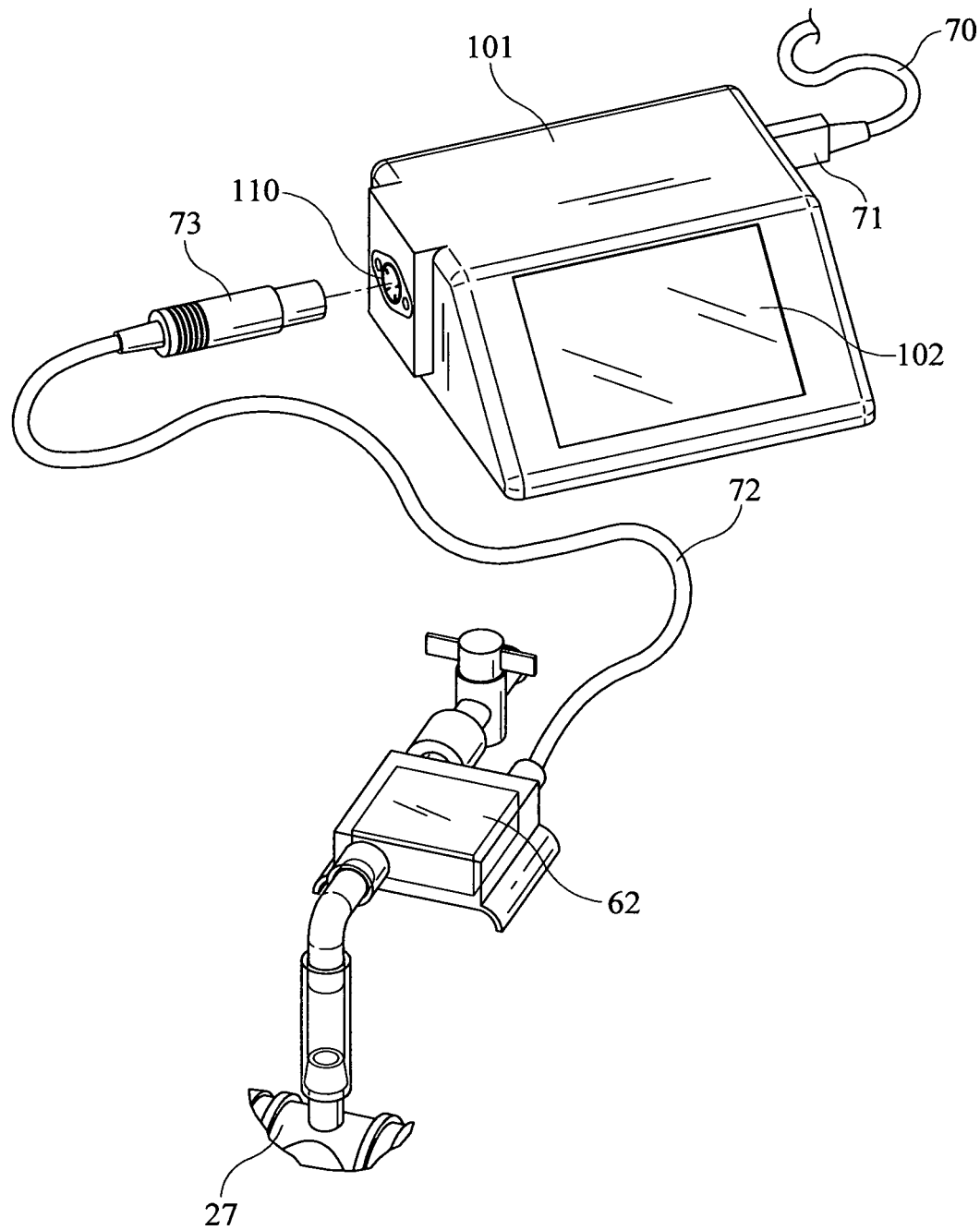
FIG. 8 is a partial view of a connector and a perspective view of a pressure sensor and a processing unit, according to multiple embodiments and alternatives.

FIG. 3 also shows an exploded view of pressure sensor 62, which includes female connector 65 (to receive and attach to the pressure sensor joint 25) and pressure sensor release valve 68. In some embodiments, the pressure sensor 62 connects to the processing unit 101 via pressure sensor wire 72. As best illustrated in FIG. 8, in some embodiments pressure sensor wire 72 includes a plug 73 that is received in plug receiver 110 of processing unit 101. In other embodiments, the pressure sensor 62 and the other components of the respiratory training device 5 are wirelessly connected to another device.

For illustrative (and non-limiting) purposes, the present embodiments are described with a pressure sensor 62 having a molded body with a pressure sensing chip affixed into a compartment in the molded body. In some embodiments, this chip contains a micro-diaphragm that detects changes in pressure. The micro-diaphragm and flow path are separated by a "dielectric silicon" that 1) can transmit force (pressure) from the flow path to the micro-diaphragm while 2) providing isolation of the flow path from the micro-diaphragm. This sensor assesses a flow path opening of about ~4 mm diameter that runs throughout the entire molded body. Furthermore, in some embodiments, the pressure sensor 62 operates by generating a voltage output that is proportional to pressure. However, any number of pressure sensors may be used as are well known to persons of ordinary skill in the art. According to current embodiments, a preferable pressure sensor is affordable, highly accurate, and light-weight.

Figure 4:
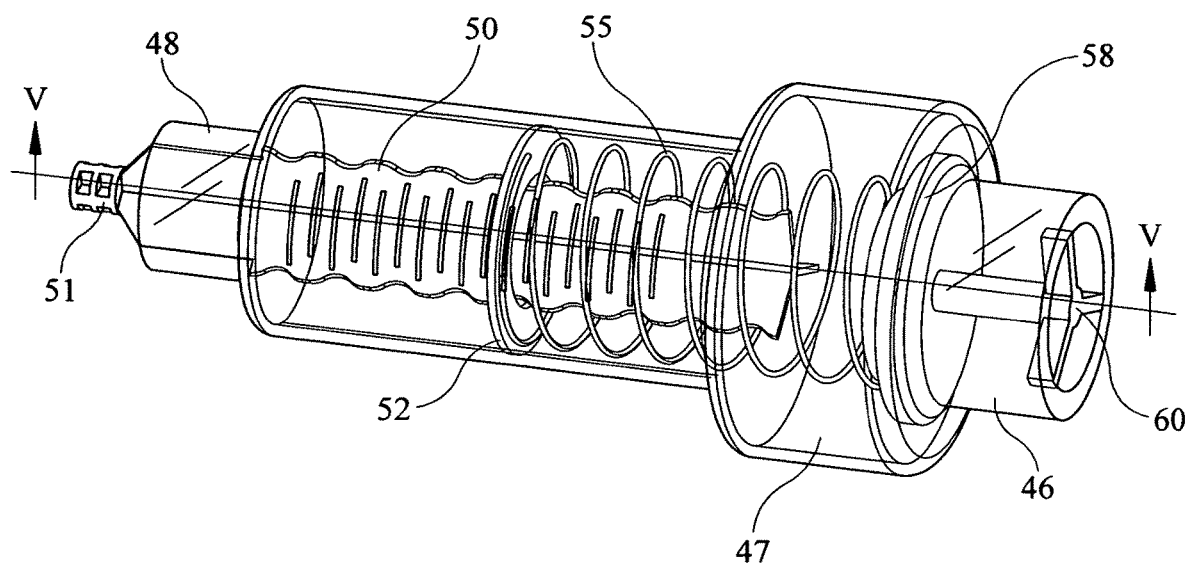
FIG. 4 is a perspective view of a hollow tube that could be used as either an inspiratory or expiratory trainer device, according to multiple embodiments and alternatives.
Figure 5:
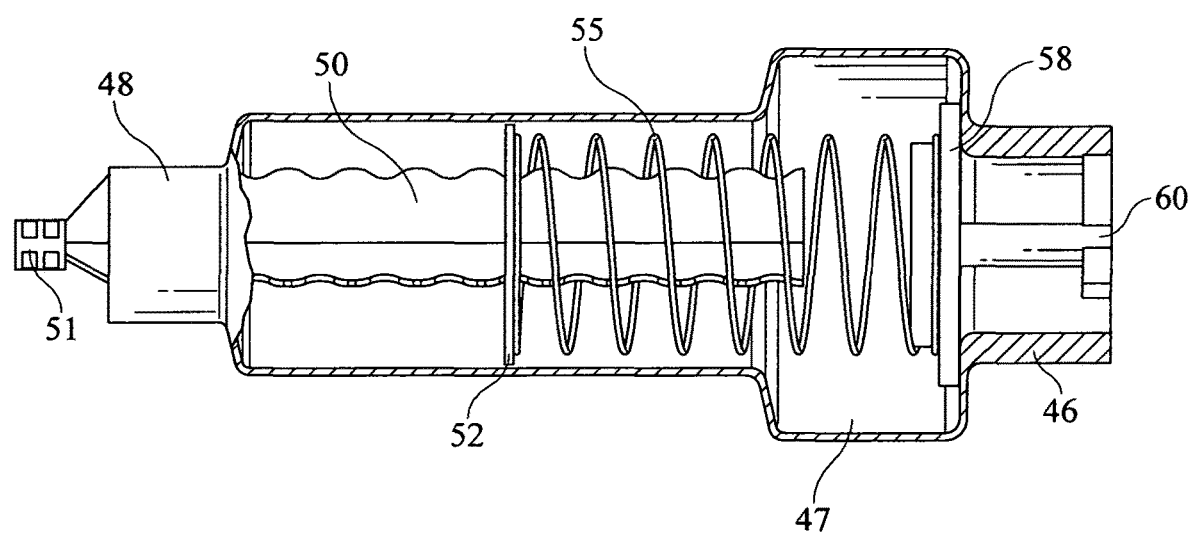
FIG. 5 is a cross-sectional view along line V-V in FIG. 4 of an inspiratory or expiratory trainer device, according to multiple embodiments and alternatives.

FIGS. 4 and 5 illustrate inspiratory training tube 42 and expiratory training tube 45. For illustrative (and non-limiting purposes), inspiratory training tube 42 consists of Philips Respironics® Device HS735-010, Andover, Mass. and expiratory training tube 45 consists of Philips Respironics® Device HS730-010, Andover, Mass. As previously noted, in some embodiments inspiratory training tube 42 and expiratory training tube 45 are identical and interchangeable, and their function in the respiratory training device 5 depends on whether the training device is connected to the inspiratory or expiratory side of connector 27. In some embodiments, the inspiratory training tube 42 can only be used for inspiration and the expiratory training tube 45 can only be used for expiration because of the unique inhale and exhale pressures and the unique pressure markings on the respective tubes.

As illustrated in FIGS. 4 and 5, in some embodiments, inspiratory training tube 42 and expiratory training tube 45 comprise neck 48, screw 50, screw handle 51, disc 52, spring 55, and one-way valve 60 with a seal 58. When used with the inspiratory training tube 42, one-way valve 60 is referred to as an inspiratory valve. Likewise, when used with the expiratory training tube 45, one-way valve 60 is referred to as an expiratory valve. In some embodiments, the outside of the tub includes gradations of the pressure values (e.g. in units of cm $H_2O$) and disc 52 illustrates the pressure resistance level within the training device. Spring 55 is connected to the seal 58 of one-way valve 60, and thus spring 55 applies pressure to the one-way valve 60. In some embodiments, inspiratory training tube 42 and expiratory training tube 45 comprise an end portion 46 with a diameter (D1) and an expanded portion 47 with a larger diameter (D2) than D1. In some embodiments, the diameter of seal 58 is larger than D1 but smaller than D2.

In some embodiments, a user can adjust the pressure settings of inspiratory training tube 42 and expiratory training tube 45 by manual manipulation of compression springs inside the airway valves. To adjust the pressure settings, a user first removes neck 48 and manually rotates screw handle 51 of screw 50 to adjust the compression of spring 55, which in turn moves the disc 52 up or down the pressure gradations which can be marked on the outside of the tube.

As spring 55 becomes more compressed, the pre-compressed position of spring changes as the distance from a non-fixed end of the spring is shortened relative to the position of the other, fixed end of the spring. In this way, the force generated by the spring on the one-way valve 60 increases, and thus higher pressure is required to open one-way valve 60. This relationship between the compression of the spring 55, the force on the one-way valve 60, and the pressure required to open the valve is explained by Hooke's law (Equation 1), which is:

$$F=-k*X \qquad \text{(Equation 1)}$$

where "F" is force, "X" is displacement or change in distance from a non-fixed end of a spring to its other, fixed end, and "k" is a constant that is characteristic of the particular spring (sometimes expressed as a negative value in the context of a restoring force exerted by a spring). Accordingly, Equation 1 describes how restoring force F scales linearly with respect to that distance the spring is either compressed or extended. The negative sign in front of the constant indicates that the equilibrium force is in the opposite direction of the displacement, X. As X decreases, the spring compresses, which increases the force on one-way valve 60. When this compressive force increases, a greater force is required during breathing exercises to open the one-way valve 60.

Accordingly, the larger force applied over the surface area of the one-way valve 60 is known as the "cracking pressure" at which point a valve begins to open and pass fluid or air. In turn, as spring 55 becomes elongated (i.e. less compressed), less pressure is required to open one-way valve 60. In either case, flow is established through inspiratory training tube 42 and expiratory training tube 45 when an enough force is generated to overcome the force created by spring 55. When the valve opens, seal 58 of one-way valve 60 is no longer in contact with end portion 46 and air can pass through. Once flow is established through the one-way valve 60 such that seal 58 is no longer in contact with end portion 46, the valve continuously remains open as long as the force from the air flow remains above the restorative force created by spring 55. An increased pressure setting requires increased effort from the user to open the seal 58 of one-way valve 60, and this increasing difficulty represents a fundamental basis of improving respiratory performance. One of ordinary skill in the art will appreciate that various kinds of valves may be selected and used for one-way valve 60, such as a butterfly valve.

Figure 10:
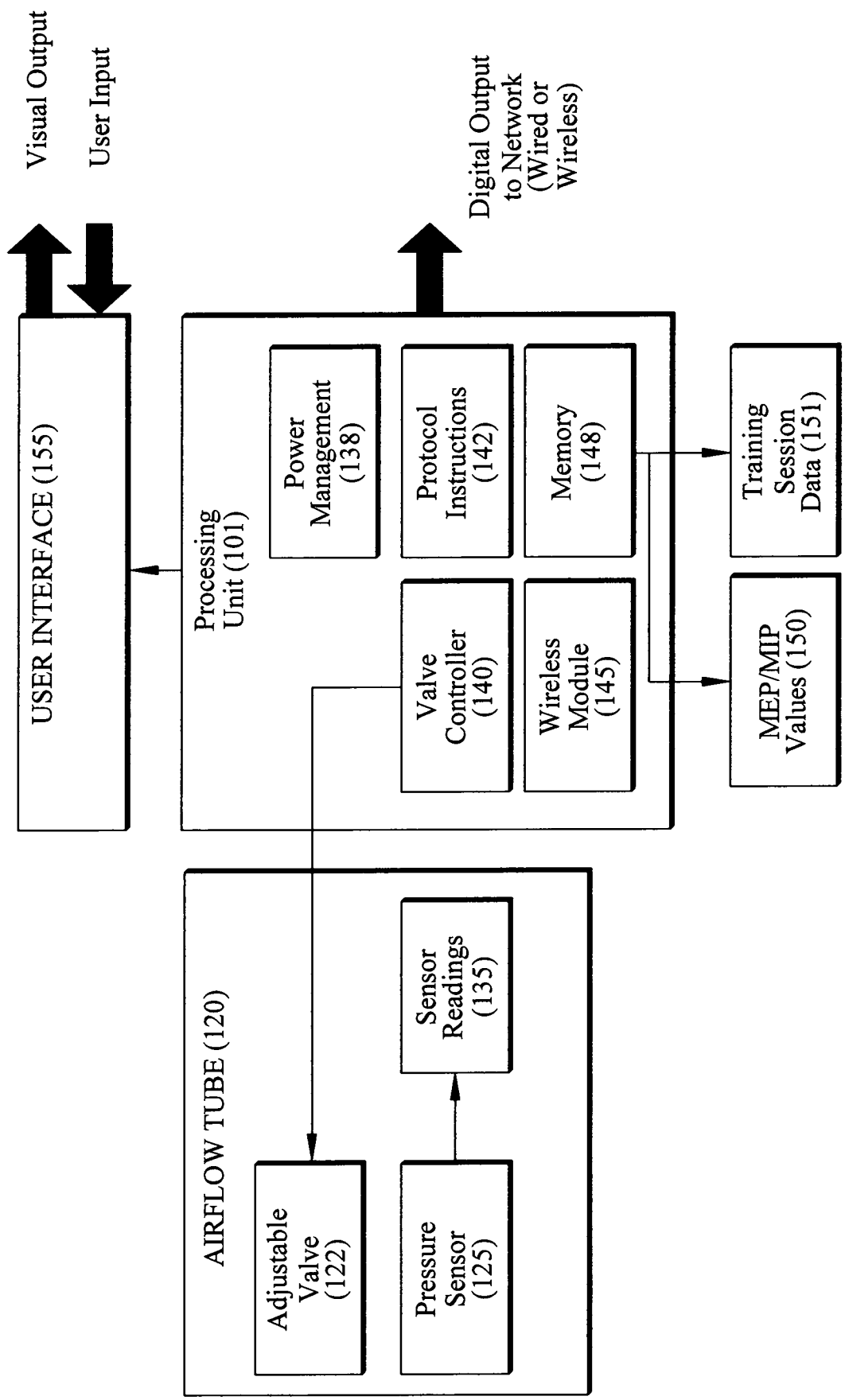
FIG. 10 is a block diagram illustrating a control device system for data acquisition, recording, storage, retrieval and display functions, according to multiple embodiments and alternatives.
Figure 11:
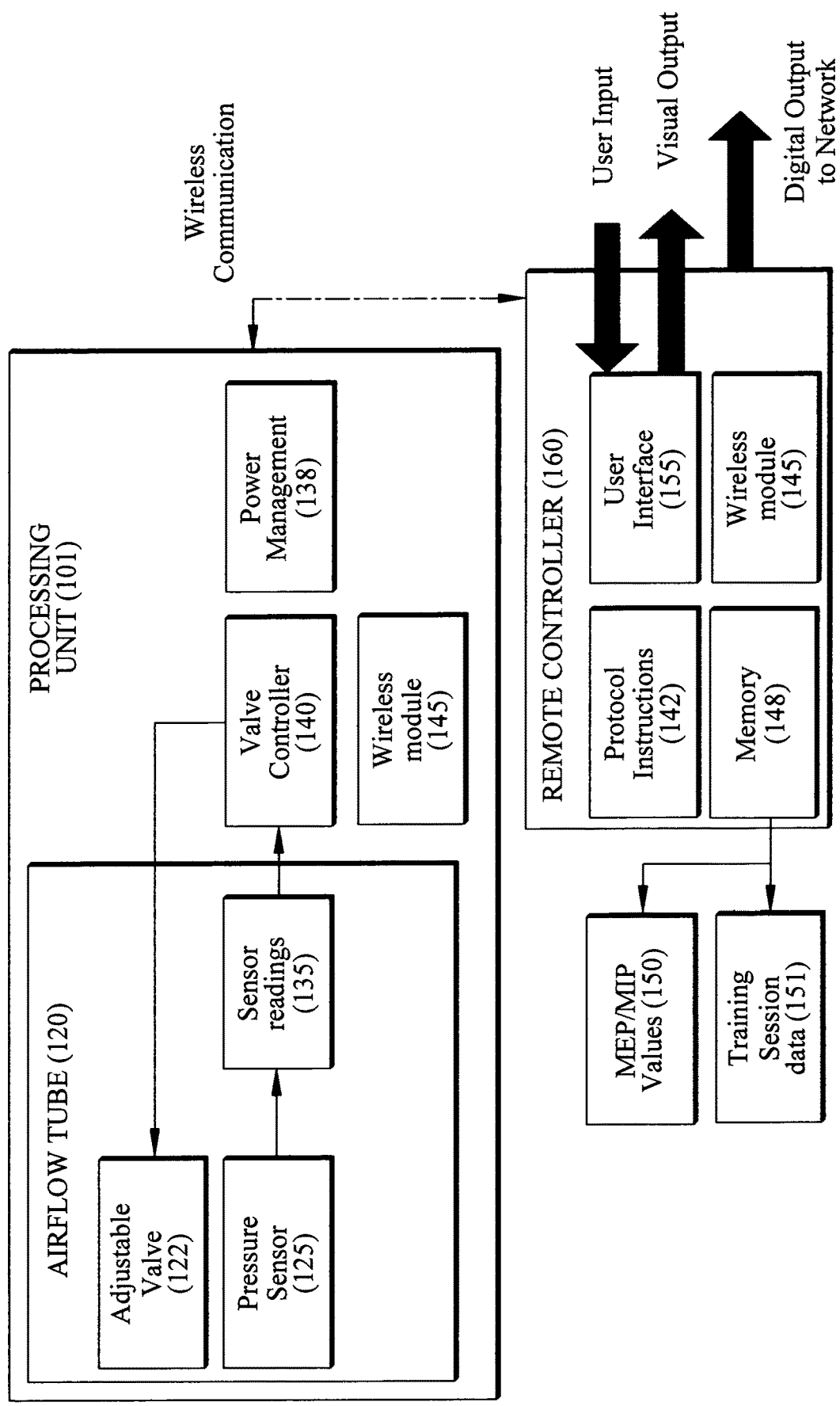
FIG. 11 is a block diagram illustrating a control device system for data acquisition, recording, storage, retrieval and display functions wherein a respiratory training device communicates wirelessly with a remote controller, according to multiple embodiments and alternatives.

As illustrated in FIGS. 10 and 11, in some embodiments processing unit 101 includes a valve controller 140 that can be adjusted by the user to change the resistance level in the inspiratory training tube 42 and expiratory training tube 45, i.e., to increase or decrease resistance. In this embodiment, the valve controller 140 is electromechanically connected to adjustable valve 122. A user changes the resistance level by manually entering the threshold pressure setting into processing unit 101 through user interface 155, and the valve controller 140 changes the adjustable valve to the user's input entry accordingly.

Figure 6:
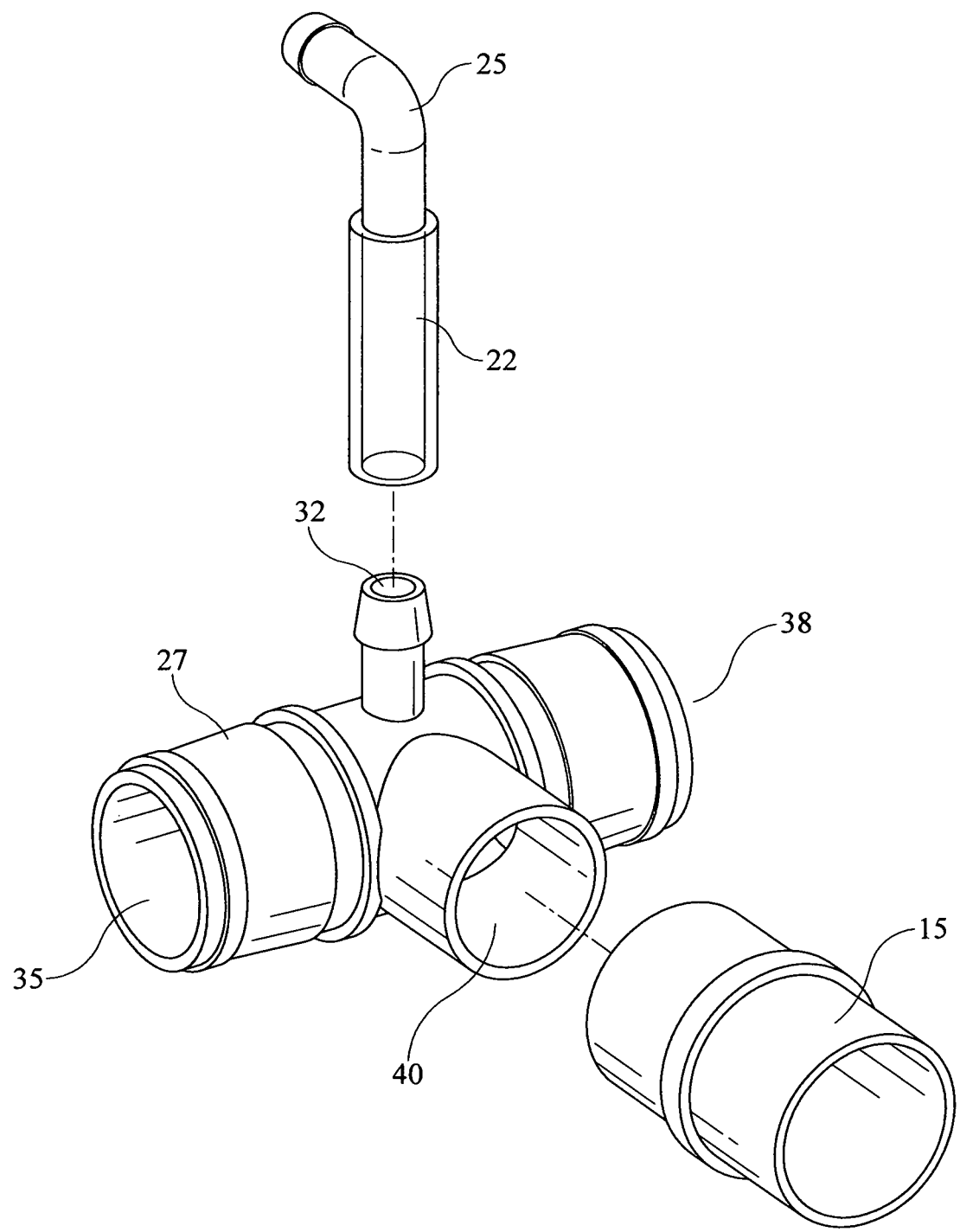
FIG. 6 is an exploded view of a connector for a respiratory training device, according to multiple embodiments and alternatives.

As shown in FIG. 6, connector 27 includes pressure port 32, expiratory training tube port 35, inspiratory training tube port 38, and mouthpiece port 40. For illustrative (and non-limiting purposes), an exemplary connector 27 is a Carefusion® (Skokie, Ill.) U/Adapt-IT "T" Part Number 004051. Pressure port 32 receives pressure sensor adapter 22, which is connected to pressure sensor 62 via pressure sensor joint 25. Inspiratory training tube port 38 receives inspiratory training tube adapter 18, which connects to inspiratory training tube 42. Expiratory training tube port 35 receives expiratory training tube adapter 20, which connects to expiratory training tube 45. Mouthpiece port 40 receives mouthpiece adapter 15, which connects to mouthpiece 10. Adapters (15, 18, and 20) are optional features and provided in FIGS. 3 and 6 for illustrative (and non-limiting) purposes. Connections between various parts described in this paragraph can be established through one of various techniques as known in the art, one example being forming portions of these parts to join together in an interference fit.

As previously noted, in some embodiments connector 27 includes one-way valve 30 and one-way valve 31 (best illustrated in FIG. 2) that permit air to travel only through the inspiratory training tube 42 or out the expiratory training tube 45, but not both. The position of pressure port 32 in tee connecter 27 permits the pressure sensor 62 to monitor and detect the pressure level when the user both inhales or exhales through respiratory training device 5.

Figure 7:
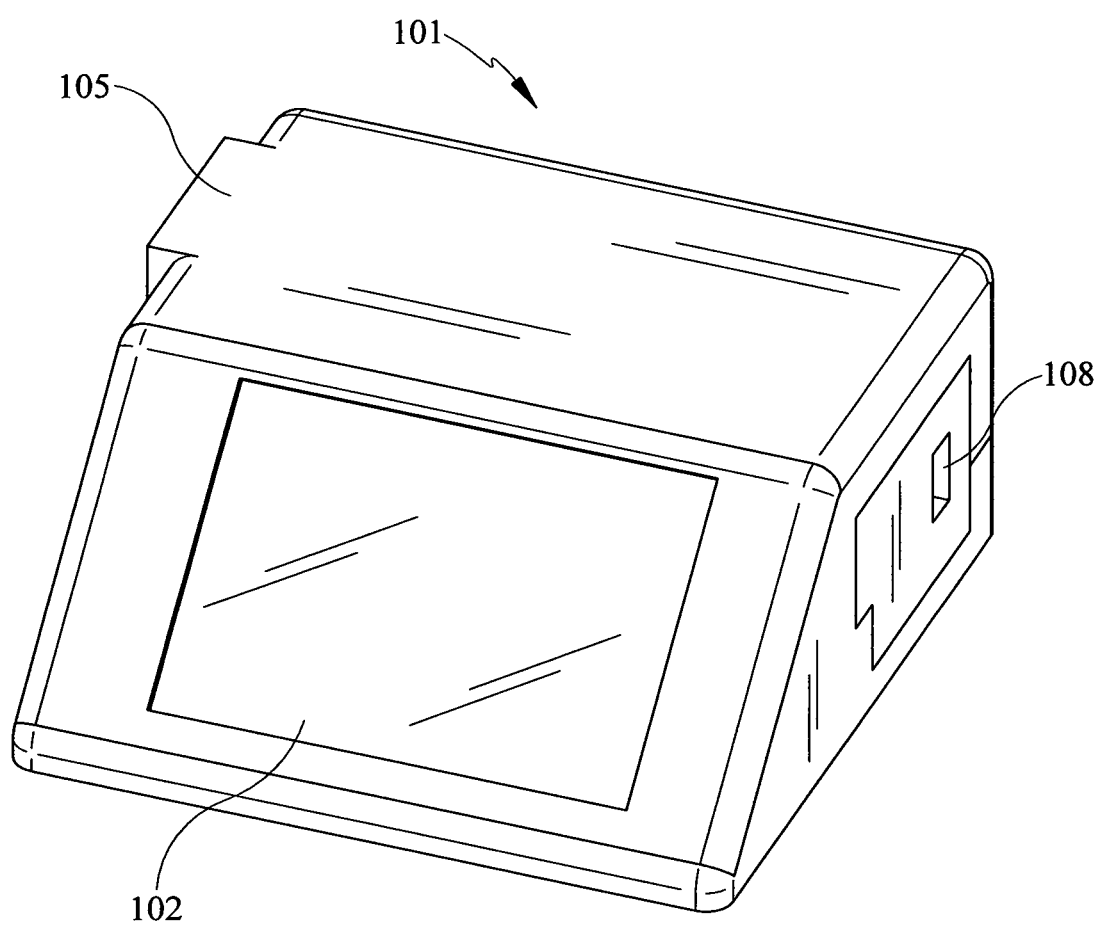
FIG. 7 is a perspective view of a user interface and processing unit, according to multiple embodiments and alternatives.

FIGS. 7 and 8 show a processing unit 101 according to multiple embodiments and alternatives. Processing unit 101 includes enclosure 105, USB port 108, touchscreen 102, plug receiver 110, and memory card slot 112 (not shown). In some embodiments, USB port 108 receives an external transmission wire 70 with a USB plug 71 that can attach to a computer or other device. Any number of ports can be built into processing unit 101 as are well known to persons of ordinary skill in the art. For users with spinal cord injuries that cannot easily manipulate their hands and fingers, touchscreen 102 is helpful in reviewing pressure activity during a training session, the results of the training session and controlling respiratory training device 5. In addition, in some embodiments the processing unit 101 provides audible feedback to the user. Conventional respiratory training devices are typically rudimentary and provide no feedback to the user. On the other hand, the processing unit 101 according to current embodiments provides visual and audio feedback to inform the user of their training level, which is a key component in implementing a training protocol. In some embodiments, the processing unit 101 converts the voltage output generated by the pressure sensor 62 to a pressure value that represents the air pressure data transmitted to the processing unit. In some embodiments, processing unit 101 also calculates the user's respiratory rate from the generated air pressure data. The respiratory rate is the rate at which breathing occurs and is usually measured in breaths per minute.

As will be discussed in more detail below, in some embodiments the control device system 100 contains hardware and software features that provide for data acquisition, recording, storage, retrieval and display functions for airway pressure monitoring data to provide functional evaluation, progress monitoring, and diagnostic features.

Figure 9:
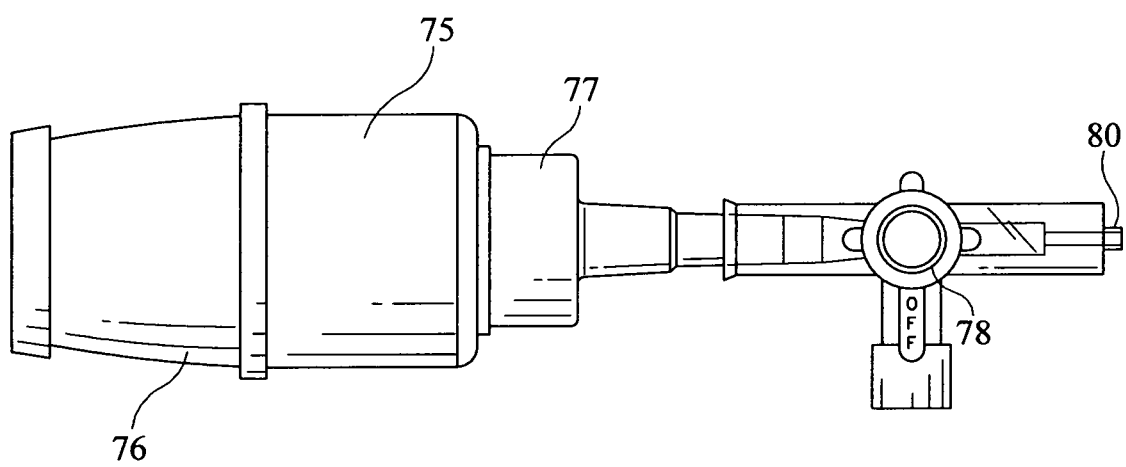
FIG. 9 is a plan view of an attachment for determining the maximum inhale and maximum exhale pressure of a user, according to multiple embodiments and alternatives.

The respiratory training device 5 provides a mode to calculate a user's maximum expiratory pressure (MEP) and maximum inspiratory pressure (MIP), and a respiratory training mode as the user inhales and exhales through the breathing apparatus. The MEP refers to the maximum pressure that a user can generate when exhaling and MIP refers to the maximum pressure generated by a user when inhaling. To obtain a user's MEP value, attachment 75 (shown in FIG. 9) is attached to expiratory training tube port 35 and control device system 100 guides the user through this mode to obtain the MEP value. To obtain the MIP value, attachment 75 is attached to inspiratory training tube port 38 and control device system 100 guides the user through this measurement. According to present embodiments, attachment 75 (shown in FIG. 9) can be connected to respiratory training device 5 to measure and record the maximum pressures of inhalation and exhalation that a user can produce. In some embodiments, attachment 75 includes first member 76, second member 77, adjustable valve 78 and extension 80 to attach to connector 27. In some embodiments, attachment 75 only permits the passage of air in one direction, it restricts air flow, and facilitates collection of airway pressure data a user produces.

As discussed below, training target pressure values for the respiratory training mode may be developed from the MEP and MIP values. In the respiratory training mode, the user inhales and exhales through respiratory training device 5 with both the inspiratory training tube 42 and expiratory training tube 45 attached. In this mode, the respiratory training device 5 functions like a spirometer, which is a device for measuring the volume of air inhaled and exhaled through the lungs. In the training mode, the inspiratory training tube 42 and expiratory training tube 45 are manually adjusted to match training target pressure values determined from the MEP/MIP mode. While performing the respiratory training mode, a user inhales and exhales through respiratory training device 5, cracking one-way valves 60, and works to maintain set target pressure values. The user interface of control device system 100 provides visual feedback to the user during training mode, and in some embodiments it lights on-screen LEDs if the user is reaching the training target values.

FIG. 10 is a block diagram depicting the data acquisition, recording, storage, retrieval and display functions of control device system 100, according to multiple embodiments and alternatives. The portion of FIG. 10 associated with airflow tube 120 (i.e., a portion of a respiratory training device through which air travels and is monitored, such as inspiratory training tube 42, expiratory training tube 45) depicts one or more volumes within which are positioned one or more sensors 125 which may include pressure sensor 62 as a non-limiting example). Such sensors generate sensor readings 135 which measure and track conditions inside an airflow tube 120.

In some embodiments, user interface 155 depicts the component that provides a visual output to the user and receives user input. As a non-limiting example, touchscreen 102 serves as a user interface in the embodiments illustrated in FIG. 1. As illustrated in FIGS. 13-20, user interface 155 guides users through various training sessions, displays results, and receives input from the user. As desired, an app may be provided that can be downloaded and executed upon a smart phone, tablet, personal computer, laptop, mobile device or similar device that guides the user, controls the respiratory device, and keeps track of performance and progress.

The block associated with processing unit 101 depicts the processing unit within which is positioned power management 138 to provide power to the processing unit 101 and respiratory training device 5 (such as battery powered, plugged into an outlet, etc.). Optionally, a power source for one or both of these components is a rechargeable lithium-ion battery. In some embodiments, processing unit 101 is configured to write and record time-stamped MEP/MIP and training data to local storage (e.g., microSD memory card) for later retrieval, and switch into sleep mode between uses to save power. Various alternative forms of memory as known in the art can be used for storage. In current embodiments, processing unit 101 includes valve controller 140 which is electromechanically connected to adjustable valve 122. A user can change adjustable valve 122 by manually inputting a particular resistance value into user interface 155, which in turn causes the valve controller 140 to change adjustable valve 122. Such a sequence could be programmed into the user interface on a screen. For example, an actuator (not shown) may be assigned to each adjustable valve 122 and will respond to electronic commands from a processor, microprocessor, or microcontroller connected to the processing unit 101, which execute computer-readable program instructions or suitable program logic. In some embodiments, a first actuator is positioned to adjust the inspiratory valve to change a first resistance to movement of air along the first flow path and a second actuator is positioned to adjust the expiratory valve to change a second resistance to movement of air along the second flow path.

As reflected in FIG. 10, processing unit 101 may include protocol instructions 142 to control the various functions of the respiratory training device 5, such as receiving and processing user input, guiding a user through a therapy session with prompts, informing user interface 155 to display results and device functions, and so forth. In some embodiments, processing unit 101 may also include a real-time clock (not shown) to record the date and time when a user utilizes the device, and to assist the user in monitoring their progress over time. Processing unit 101 consists of memory 148 to record and store therapy sessions and provide various processing unit 101 functions. As previously noted, in current embodiments respiratory training device 5 includes two modes: a MEP/MIP mode which generates MEP/MIP values 150 and a training session that generates training session data 151. Processing unit 101 is involved with providing digital output via a network through a wired connection or wireless module 145.

As shown in FIG. 11, in some embodiments control device system 100 includes an airflow tube 120 positioned within a processing unit 101 which wirelessly communicates with a remote controller 160. In FIG. 11, airflow tube 120 includes adjustable valve 122 and pressure sensor 125. The sensor readings 135 generated by one or more sensors are sent to valve controller 140 positioned within processing unit 101. In some embodiments, a user can change adjustable valve 122 by manually providing input via user interface 155 of remote controller 160. In some embodiments, user input is in turn wirelessly communicated to valve controller 140 that is connected to electromechanically adjustable valve 122. In some embodiments, a low-power, energy-conserving, battery-powered microcontroller, or like components, is located within or operationally connected to the bi-directional airflow assembly 8 for storing and executing program code to initiate actuation of each valve 60. Processing unit 101 also includes power management 138 and wireless module 145 to provide wireless communication with remote controller 160. As a non-limiting example, remote controller 160 is a mobile phone or a tablet with an app programmed to wirelessly communicate with processing unit 101. In FIG. 11, remote controller 160 includes protocol instructions 142, wireless module 145, memory 148, and user interface 155. In current embodiments, remote controller 160 produces MEP/MIP values 150 and training session data 151.

Figure 12A:
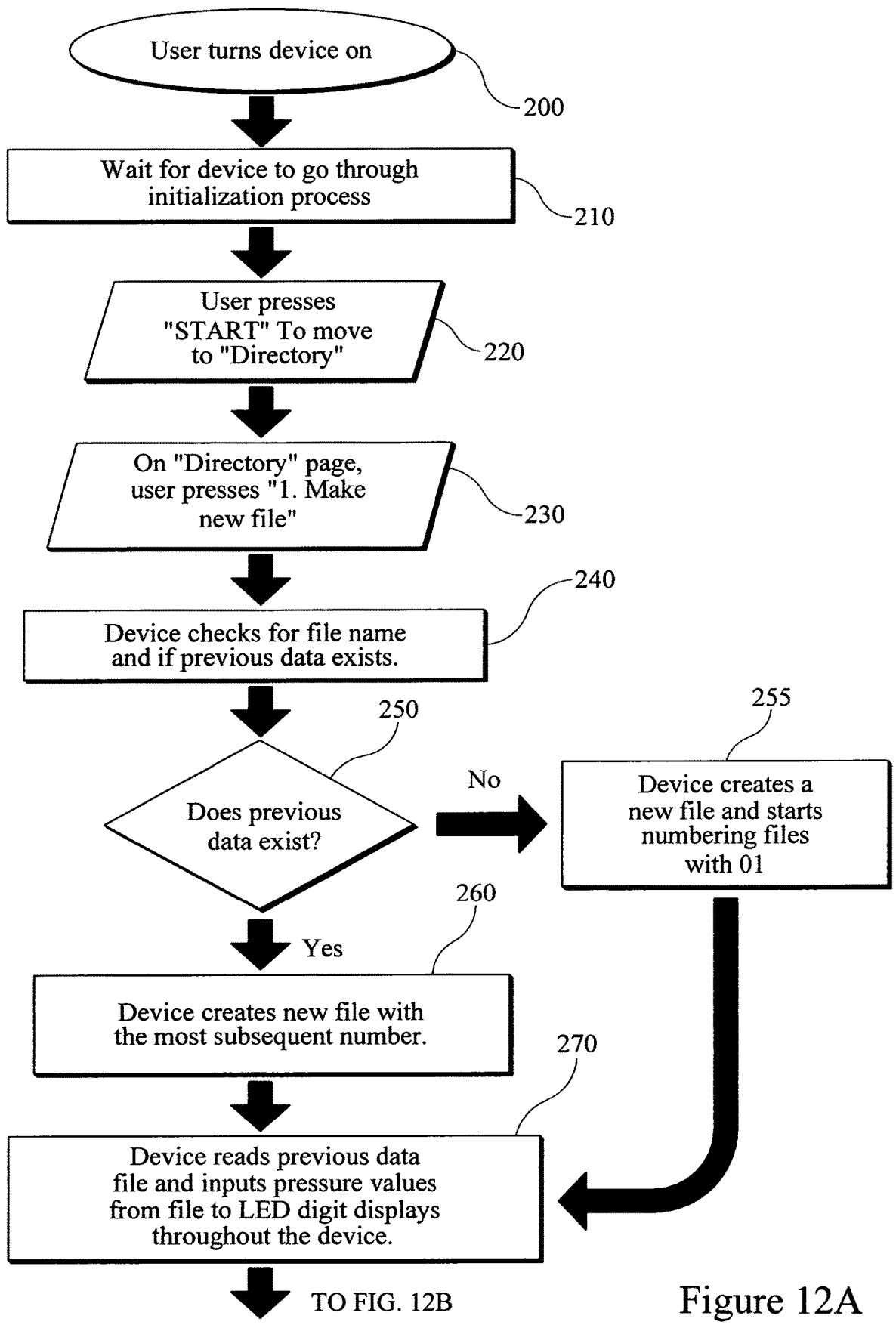
FIG. 12A-12C is a flow chart illustrating the operation processes of a respiratory training device, according to multiple embodiments and alternatives.
Figure 12B:
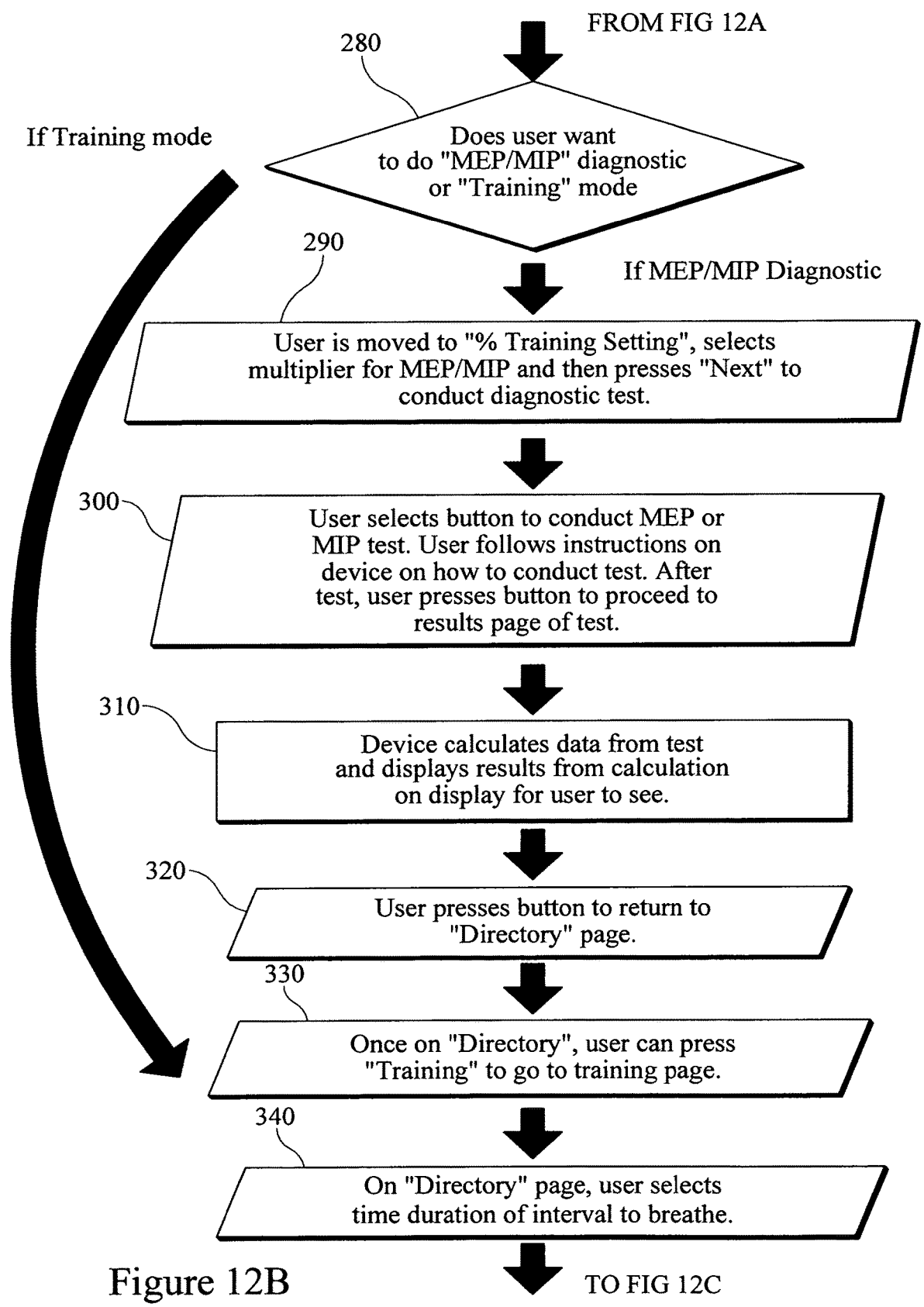
Figure 12C:
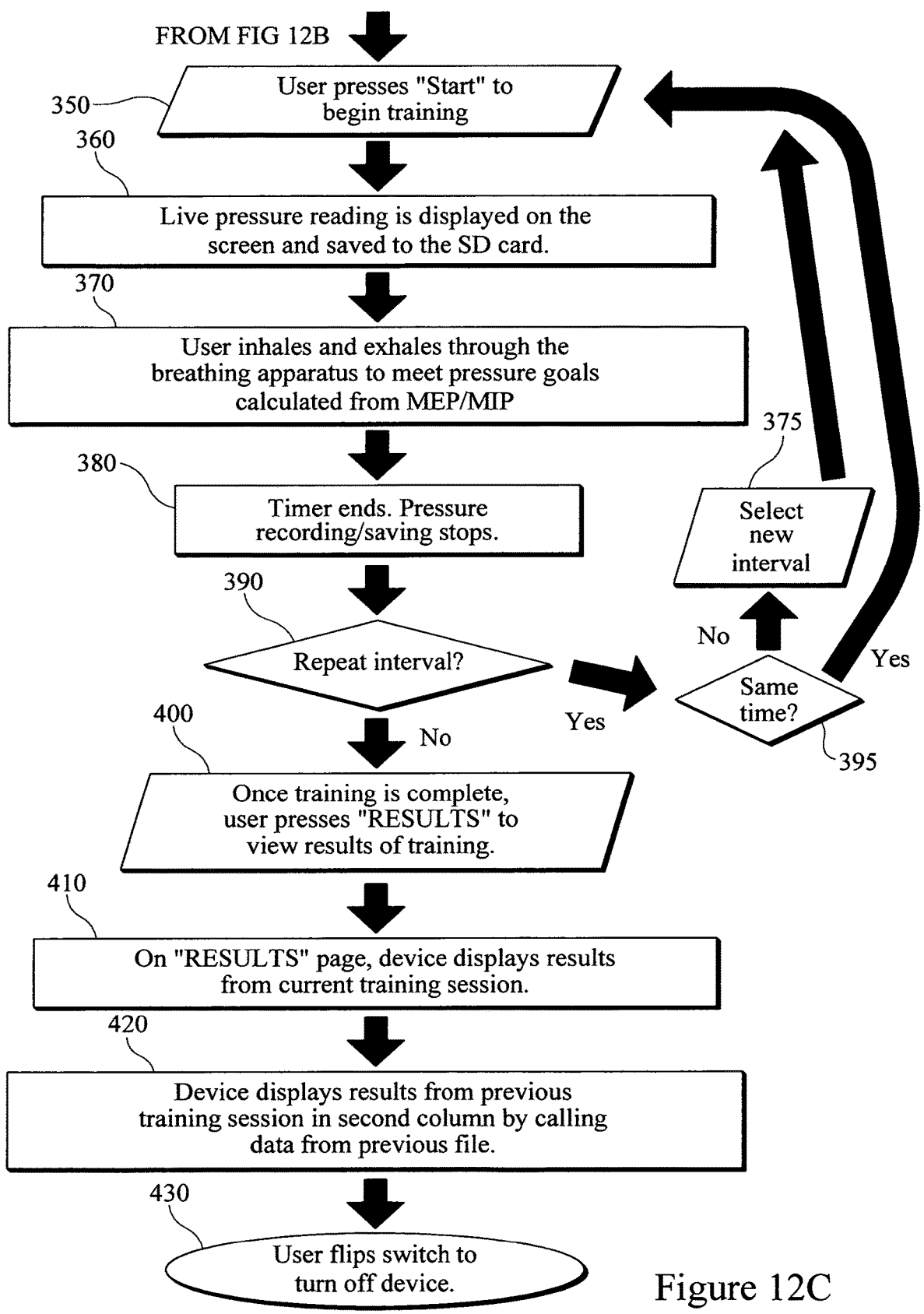
Figure 13:
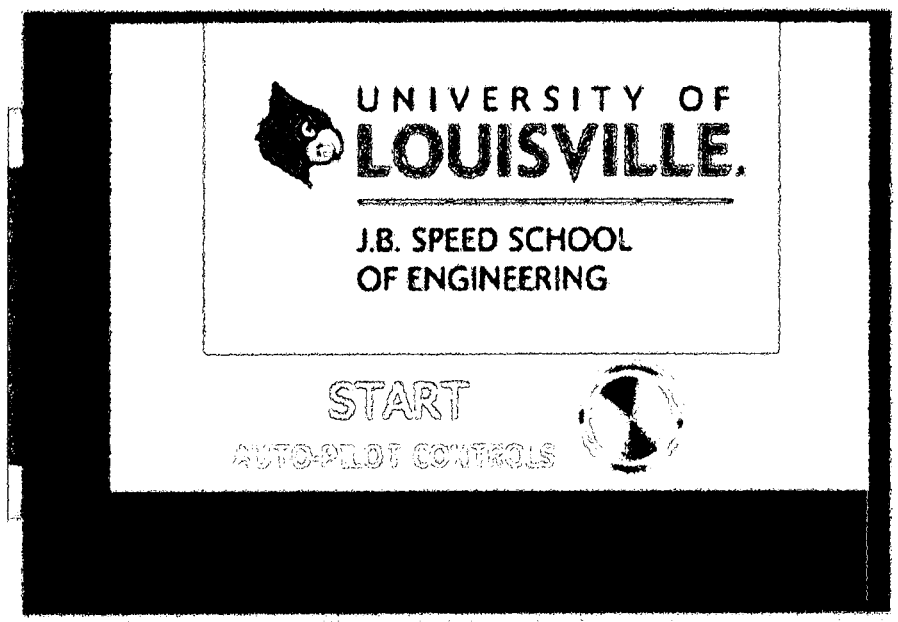
FIG. 13 shows a portion of the user interface display of a respiratory training device, according to multiple embodiments and alternatives.
Figure 14:
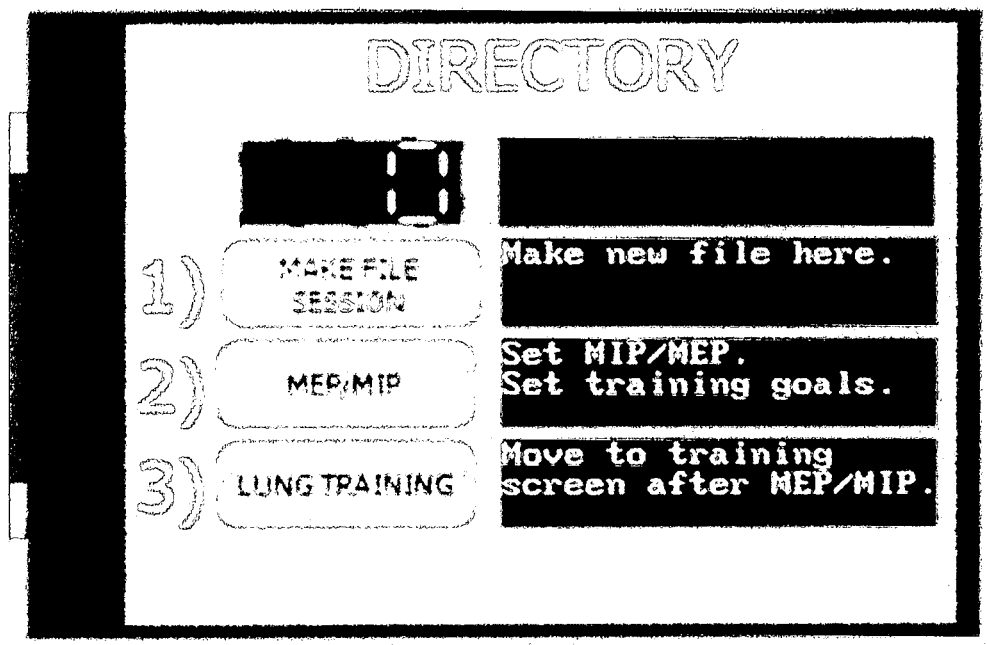
FIG. 14 shows a portion of the user interface display of a respiratory training device, according to multiple embodiments and alternatives.

FIG. 12A-12C illustrate the operation processes of the respiratory training device 5 utilizing control device system 100, according to multiple embodiments and alternatives. FIGS. 13-20 illustrate various user interface displays of the operation processes on a touchscreen display (as a non-limiting example). The various user interface displays illustrate the visual output of the device and user input of the respiratory training device 5 utilizing control device system 100, according to multiple embodiments and alternatives. It will be appreciated that the scope of embodiments is not limited to and does not otherwise require the arrangement of components illustrated in FIGS. 10 and 11, is not limited to and does not otherwise require the operation processes illustrated in FIG. 12A-12C, and is not limited to the user interface displays illustrated in FIGS. 13-20.

As shown in FIG. 12A-12C, after the respiratory training device 5 is turned on (200), step 210 is for performing an initialization process to verify the real-time clock is functioning and a memory card (such as an SD card) is inserted into memory card slot 112. Once the checks at step 210 pass, the user is notified to press "Start" at step 220 (see user interphase illustrated at FIG. 13). On the Directory page (see FIG. 14), the respiratory training device 5 runs an initial calibration step (220) to zero any initial pressure sensor offsets which account for the current location of the device and environmental effects on pressure sensor 62. After step 220, the user presses "Make File Session" at step 230 to create a new file for the current session (see FIG. 14). Next, the device performs a file-check on file names that exist in the memory (step 240). If previous data does not exist (250), the device creates a new file and starts numbering files with 01 (step 255). If previous data does exist, the device proceeds to step 260 and creates a new file with the most subsequent number. At step 270, the respiratory training device 5 reads the previous data file and inputs those previous pressure values from the memory file to LED digit displays throughout the device (see e.g. FIG. 18). At step 280, the user must select if they want to proceed with the MEP/MIP mode or training mode (see FIG. 14).

Figure 15:
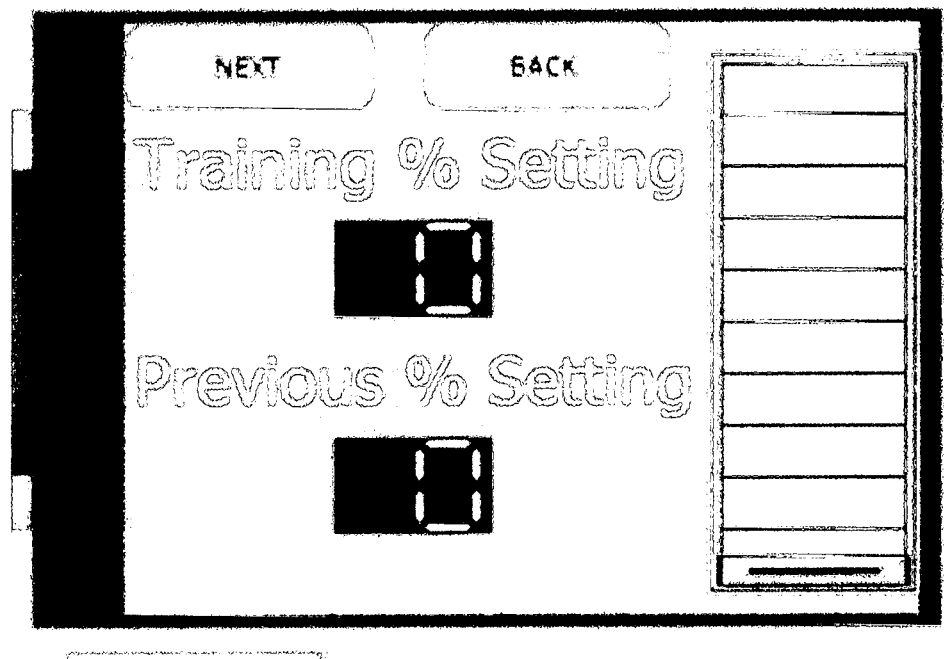
FIG. 15 shows a portion of the user interface display of a respiratory training device, according to multiple embodiments and alternatives.
Figure 16:
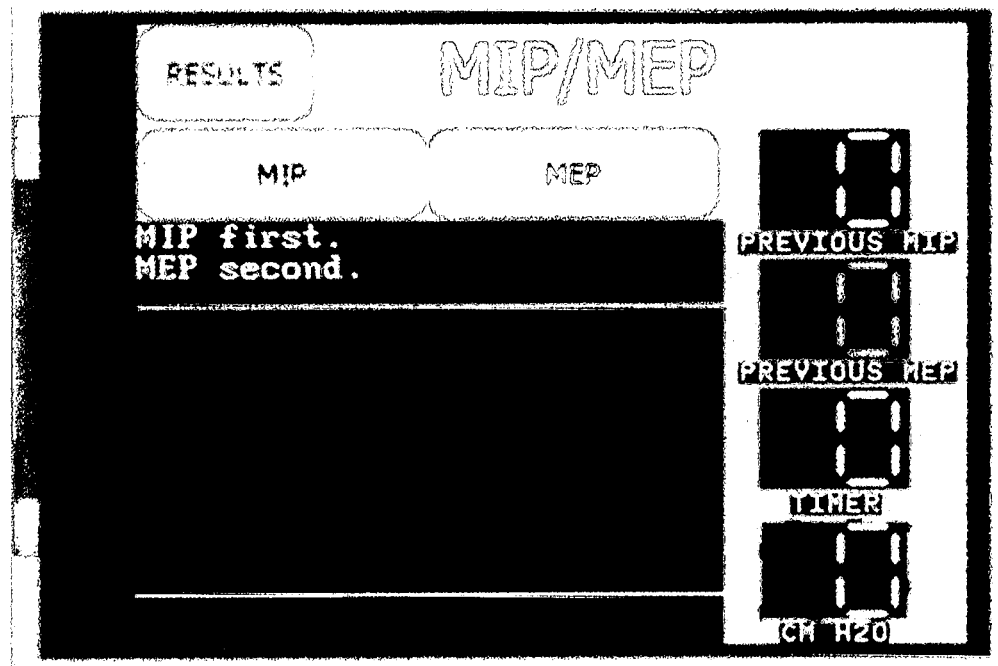
FIG. 16 shows a portion of the user interface display of a respiratory training device, according to multiple embodiments and alternatives.
Figure 17:
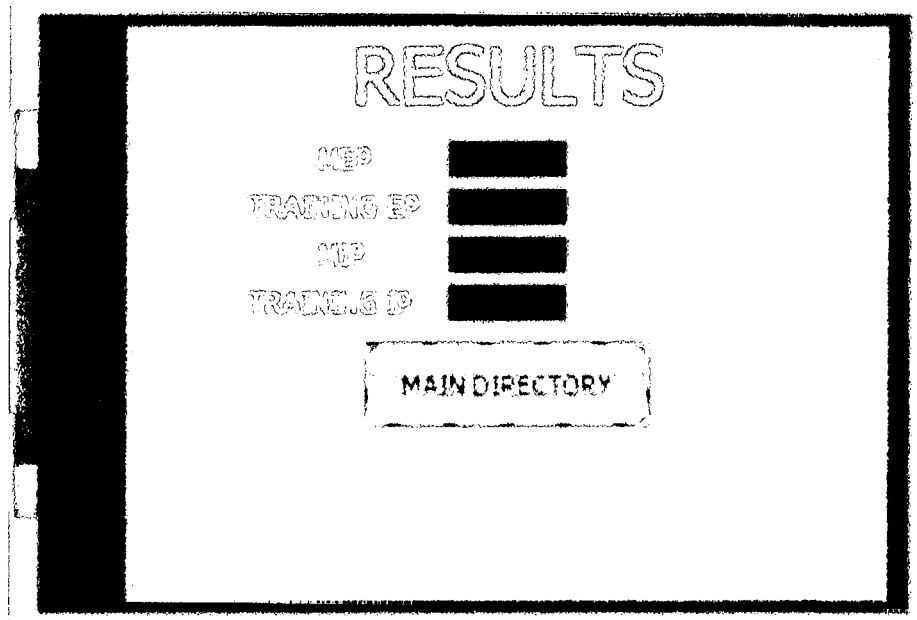
FIG. 17 shows a portion of the user interface display of a respiratory training device, according to multiple embodiments and alternatives.
Figure 18:
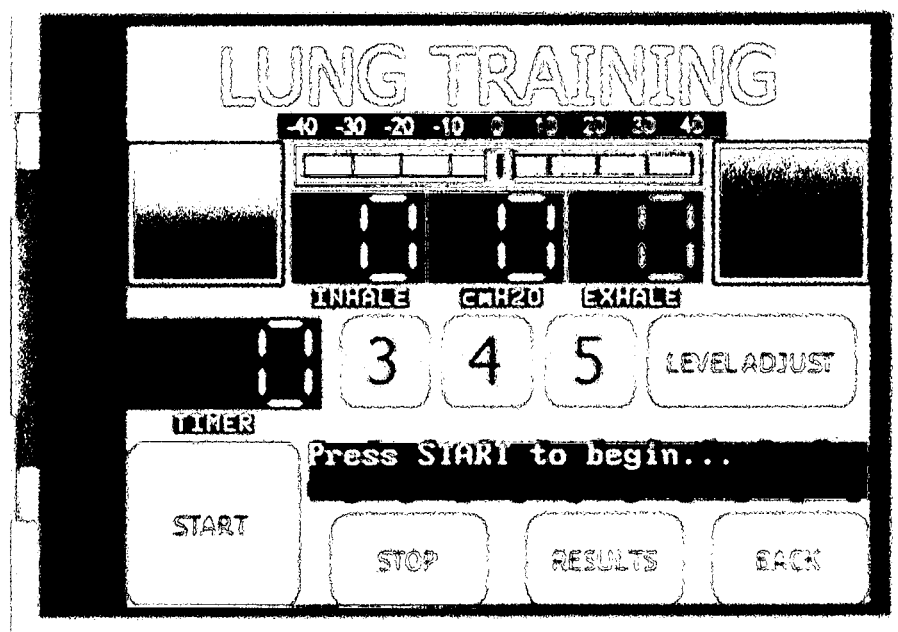
FIG. 18 shows a portion of the user interface display of a respiratory training device, according to multiple embodiments and alternatives.
Figure 19:
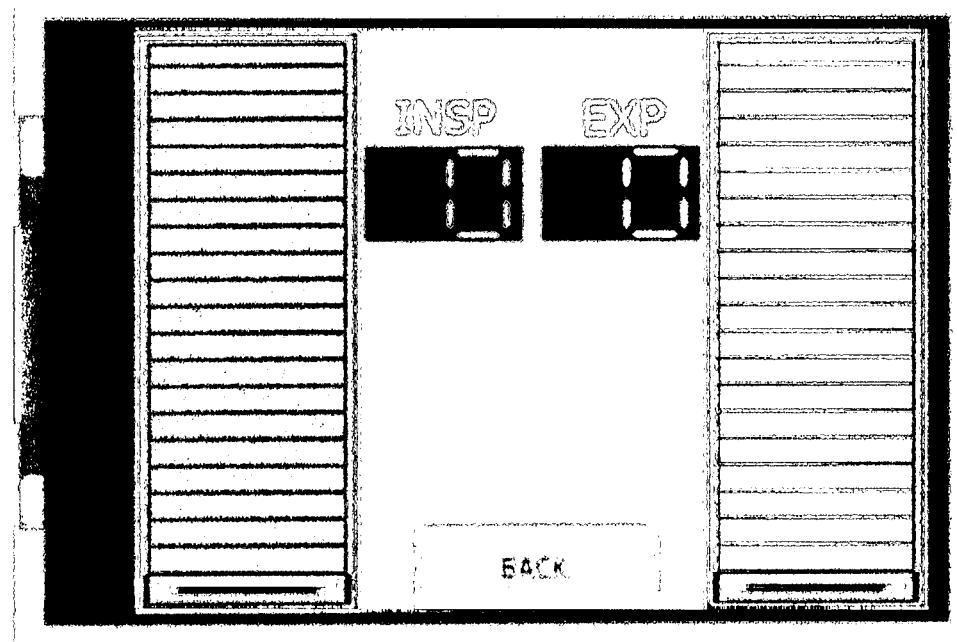
FIG. 19 shows a portion of the user interface display of a respiratory training device, according to multiple embodiments and alternatives.
Figure 20:
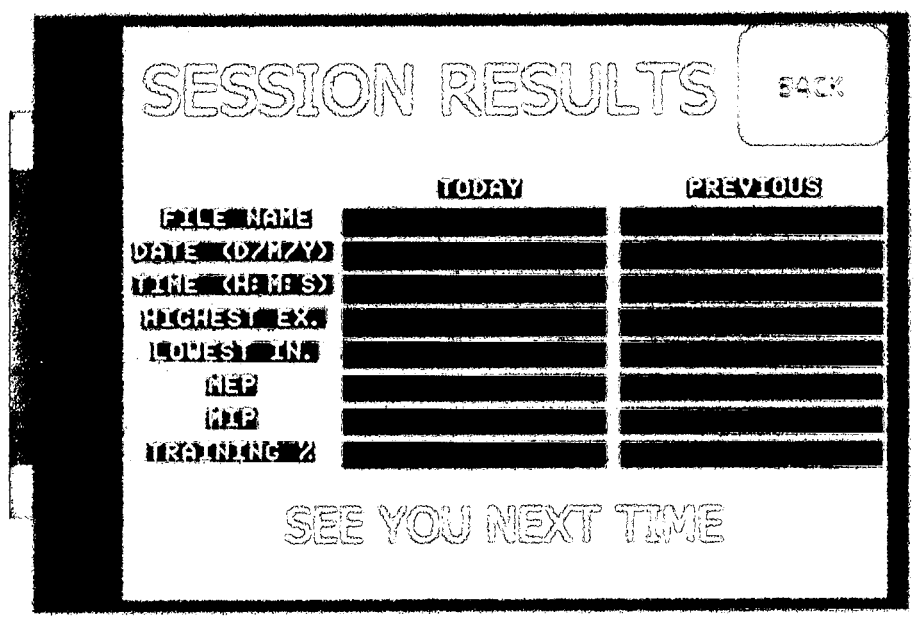
FIG. 20 shows a portion of the user interface display of a respiratory training device, according to multiple embodiments and alternatives.

As shown in FIG. 12B, if the user proceeds with the MEP/MIP mode (e.g. by selecting the "MEP/MIP" virtual button shown in FIG. 14), the user is moved to "% Training Setting" at step 290, selects a multiplier for the MEP/MIP mode and then presses "Next" to conduct the diagnostic test (e.g. see "Next" virtual button in FIG. 15). In some embodiments, the user selects the multiplier by adjusting a "Training % Slider" virtual button illustrated to the right of the "Training % Setting" and "Previous % Setting" in FIG. 15. According to multiple embodiments and alternatives, the purpose of a "Training % Slider" is to set the multiplier for the MEP/MIP mode which will generate the target pressures that the user needs to reach in the training mode. For example, if the MEP is 100 psi and the user wants to train at 20%, the device will change the target pressure to 20 psi. While a user can select any training percentage, a clinician or anyone who understands how to strengthen respiratory muscles, will know the optimal training percentage of MEP/MIP that a user should select to improve respiratory fitness during training. In some embodiments, the MEP/MIP values 150 are relayed to the clinician who then informs the user what resistance to select on the manual resistance valves of the inspiratory training tube 42 and the expiratory training tube 45.

On the MEP/MIP page (illustrated in FIG. 16), the user will select the button to conduct the MEP or MIP test (300). In a clinical setting, a clinician prepares the respiratory training device 5 with the attachment 75 and instructs the user on how to inhale or exhale for the test. In a home setting, the respiratory training device 5 provides instructions to the user on connecting attachment 75 and conducting the MEP/MIP tests. Once attachment 75 is connected, the clinician or user will press "MIP" (see FIG. 16) and follow the instructions on when to inhale. Once the inhalation test is complete, the clinician or user will switch attachment 75 to the expiratory side, and instruct the user on how to exhale through the apparatus. Either the clinician or user can press "MEP" to begin the test (see FIG. 16). Step 310 is for calculating the data from the MEP/MIP test and displaying the results from the calculation on the user interface (see FIG. 17). On the "Results" page illustrated in FIG. 17, the user interface displays MEP and MIP values from the test and the calculated training values for the training mode from the "% Training Setting" inputted by the user. From the "Results" page, the user presses a button to return to "Directory" page (320).

As shown in FIG. 12B, the user can press "Training" on the "Directory" page to begin the training mode (330). In some embodiments, training values are displayed next to LED indicators to provide additional visual output to the user (see e.g. FIG. 18). For example, in non-limiting embodiments the LED indicators light up green if the user's current pressure reading reaches 90% of the training value. Furthermore, a user can adjust the training values by adjusting a sliding gauge (illustrated at FIG. 19), which provides additional visual feedback for the user during the training session.

At step 340, the clinician or user will manually change the resistance settings on the inspiratory training tube 42 and the expiratory training tube 45 to match the training values. The clinician or user will then detach attachment 75 and attach both the inspiratory training tube 42 and the expiratory training tube 45 as best illustrated in FIGS. 1 and 3. Before beginning the training session, the user or clinician selects the duration of the training session and presses the corresponding button on the user interface display (340). In the embodiments illustrated in FIG. 18, a user can select between 3 to 5 minute training sessions, however it will be appreciated that any length of time for a training session may be selected. Once the timer is set, at step 350 the user presses "Start" (see virtual button shown in FIG. 18) to begin the training session.

During the training session, live pressure readings are displayed on the user interface displace and saved to the memory (360). The user inhales and exhales through the respiratory training device 5 to meet the pressure goals calculated from the MEP/MIP mode (370). Once the timer ends, at step 380 the pressure recording embodiments cease. Next, the user can repeat a training session (390). If the user desires to repeat a training session using the same time (395), the user can press the "Start" button to begin the training again (350). Alternatively, the user can select a new interval (375) and begin a new training session (350).

Once training is complete, the user presses "Results" (see virtual button illustrated in FIG. 18) to view the results of the training (400). On the "Results" page (see FIG. 20), the user interface displays the results from the current training session (410) and the results from previous training sessions by retrieving data from previous file (420). In some embodiments illustrated in FIG. 20, the "Results" page displays the date, time, highest exhale, lowest inhale, the MEP, the MIP, and the training percentage from the current session and the previous session in a second column. However, any number of results may be displayed as are well known to persons of ordinary skill in the art. Next, the user turns the device off (430) and stores it away until the next training session.

Figure 21:
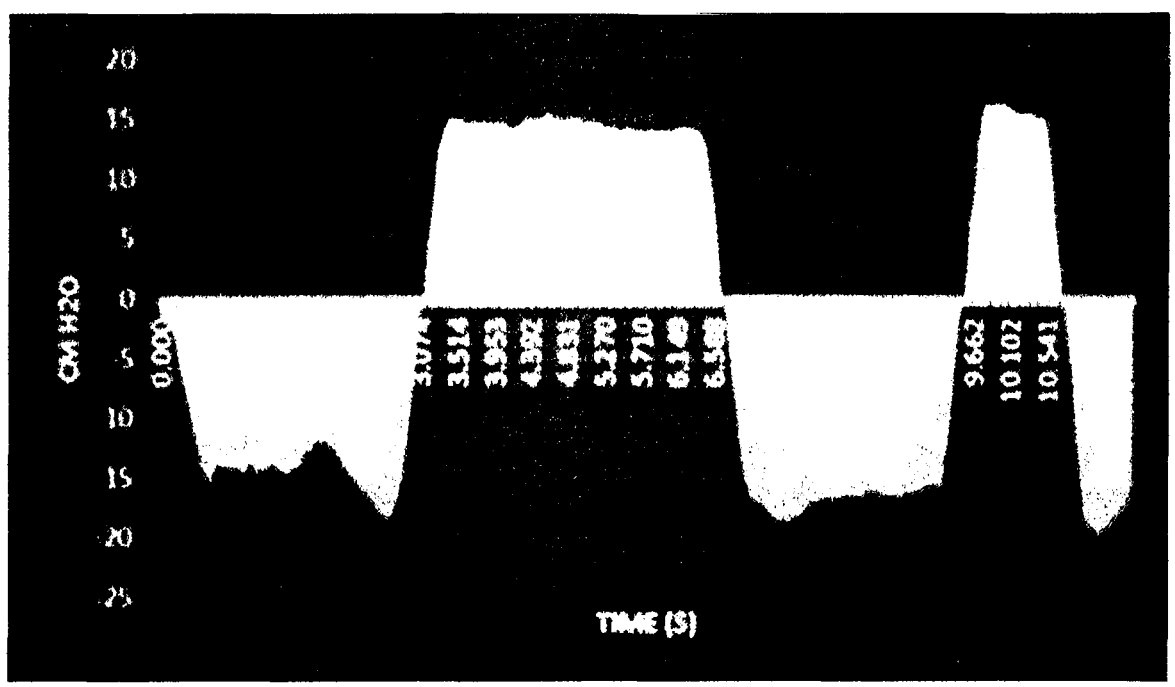
FIG. 21 provides example results of a user training session with a respiratory training device, according to multiple embodiments and alternatives.

FIG. 21 illustrates example results of a user training session with a respiratory training device 5, wherein the x column represents the time in seconds of the training session and the y column represents the pressure values in units of cm $H_2O$. As shown in FIG. 21, the respiratory training device 5 records, monitors and displays the inspiratory and expiratory pressure as the user breathes through the device. In this particular example, the length of the user's inhale and exhale greatly diminished after roughly 9 seconds of training on the device. These types of results can be used to monitor and implement respiratory training regimens.

Example 1—Verification and Validation

Pressure Test

To verify and validate the respiratory training device 5, pressure measurements using the device were compared to a Delta-Cal Transducer Similar and Tester (Utah Medical Products, Salt Lake City, Utah). The Delta-Cal tester was connected directly to pressure sensor 62 and pressure adjusted to compare with the pressure measurements in respiratory training device 5. Measurements were recorded every five minutes, for twenty minutes to characterize any drift in the measurement. Both the Delta-Cal and the respiratory training device 5 readings were recorded for comparison and device validation.

Table 1 provides the averages of data points (n=5) obtained for pressure measurements using respiratory training device 5. The average standard deviation of the respiratory training device 5 pressure measurement versus Delta-Cal measurement was 1.16 mmHg (n=11). Average percent error of the respiratory training device 5 measurements versus calibrator was 3.44% across the span of pressures measured. This percent error is larger than the 2% accuracy range rated by pressure sensor's manufacturer that covered an even larger range (0-310.29 mm Hg) versus bench testing (−50 to 50 mm Hg). This error was deemed acceptable as errors could have stemmed from calculation errors in the software.

TABLE 1

Statistics of Average Respiratory Training Device Measurements Compared to Delta-Cal Measurements

| Delta-Cal (mmHg) | Average BF (mmHg) | Std. BF | % Error |
|---|---|---|---|
| −50 | −48 | 2.33 | 4.12 |
| −40 | −38 | 1.97 | 4.41 |
| −30 | −29 | 1.48 | 4.41 |
| −20 | −19 | 0.89 | 3.68 |
| −10 | −10 | 0.49 | 4.41 |
| 0 | 0 | 0.00 | 0.00 |
| 10 | 10 | 0.49 | 4.41 |
| 20 | 19 | 0.77 | 2.94 |
| 30 | 29 | 0.89 | 2.45 |
| 40 | 38 | 1.84 | 4.04 |
| 50 | 49 | 1.64 | 2.94 |
| Average | | 1.16 | 3.44 |

Analysis of Pressure Sensor Test

The respiratory training device 5 produced a near 1:1 relationship compared to the Delta-Cal pressure standard in the pressure sensor test. Despite an average standard deviation of 1.16, and percent error of 3.44%, the larger standard deviation occurred mostly in the higher-pressure ranges of 30-50 mmHg, consistent with most common pressure and force sensors with accuracies reported as a percent of full scale. The farther the measurement from zero, the larger the error. Regardless, these larger values of pressures exceed normal inspiratory and expiratory training regimens set by the training procedures discussed herein. Regular training settings for subjects with spinal cord injury usually range from 5-20 mmHg for both expiratory and inspiratory activates. When considering only that range, deviation average drops to 0.53 and percent error falls to 3.09%. With an R-squared of greater than 0.99, it can be confidently claimed that the pressure sensor used in the respiratory training device 5 and the conversion calculations in the processing unit 101 produce accurate pressure readings regardless of the state of the sensor and produce similar results to that of the calibrated pressure reference device.

Example 2—Subject Testing

As shown in table 4, subject testing was conducted to verify the respiratory training device 5 fulfills its intended purposes as discussed herein. During this test, a volunteer (Subject A) with lower extremity paralysis was used to obtain subject data. During the test, Subject A had pressure threshold settings set to 10% of their individual MEP/MIP. Subject A performed two 10% threshold sessions. Table 4 shows the results of expiratory and inspiratory training of subject A. Deviation of expiratory pressure was calculated by finding the average pressure of all complete expiratory cycles and subtracting it from the target expiratory pressure. The deviations of inspiratory pressures were calculated in the same way.

TABLE 4

Subject A Data

| | Summary of Participant Data 10% | | |
|---|---|---|---|
| MEP | 93.00 | 93.00 | |
| Target Exp | 9.30 | 9.30 | Average |
| Average Exp | 8.77 | 7.97 | 8.37 |
| Deviation | −0.53 | −1.33 | −0.93 |
| MIP | −94.00 | −94.00 | |
| Target Insp | −9.40 | −9.40 | Average |
| Average Insp | −8.23 | −7.06 | −7.65 |
| Deviation | 1.17 | 2.34 | 1.76 |

Because the pressure sensor was validated previously by Delta-Cal, it was safe to assume that pressure values displayed on the respiratory breathing device 5 were accurate. After MEP/MIP tests were conducted, threshold valve levels were set to match target values derived from MEP/MIP.

Accordingly, the results from Example 2 illustrate the respiratory training device 5 functions for its intended purposes and provides respiratory muscle training.

It will be understood that the embodiments described herein are not limited in their application to the details of the teachings and descriptions set forth, or as illustrated in the accompanying figures. Rather, it will be understood that the present embodiments and alternatives, as described and claimed herein, are capable of being practiced or carried out in various ways.

Also, it is to be understood that words and phrases used herein are for the purpose of description and should not be regarded as limiting. The use herein of "including," "comprising," "e.g.," "containing," or "having" and variations of those words is meant to encompass the items listed thereafter, and equivalents of those, as well as additional items.

Accordingly, the foregoing descriptions of several embodiments and alternatives are meant to illustrate, rather than to serve as limits on the scope of what has been disclosed herein. The descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A respiratory device for training a user's respiratory fitness, comprising:
   a bi-directional airflow assembly comprising an inspiratory training tube, an expiratory training tube, a connector, and a mouthpiece, wherein each of the inspiratory training tube, expiratory training tube, connector, and mouthpiece has a hollow portion;
   wherein the connector establishes a first flow path through the hollow portions of the mouthpiece and the inspiratory training tube, and the connector establishes a second flow path through the hollow portions of the mouthpiece and the expiratory training tube;
   wherein the inspiratory training tube comprises an inspiratory valve permitting air entry into the inspiratory training tube, and the inspiratory training tube, connector, and mouthpiece define a first volume representing the first flow path for air drawn into the bi-directional airflow assembly when the user inhales through the mouthpiece;
   wherein the expiratory training tube comprises an expiratory valve permitting air to exit from the expiratory training tube, and the expiratory training tube, connector, and mouthpiece define a second volume representing the second flow path for air blown out of the bi-directional airflow assembly when the user exhales into the mouthpiece;
   the bi-directional airflow assembly further comprising:
      a first actuator positioned to adjust the inspiratory valve to change a first resistance to movement of air along the first flow path;
      a second actuator positioned to adjust the expiratory valve to change a second resistance to movement of air along the second flow path;
      a pressure sensor in communication with the volumes defined by the first flow path and the second flow path to obtain an air pressure data within the bi-directional airflow assembly associated with the user inhaling through, or exhaling into, the mouthpiece; and
      a processing unit configured to receive the air pressure data from the pressure sensor, connect to a display device, and transmit the air pressure data to the display device;
   wherein the air pressure data is a voltage output sensed by the pressure sensor, and the processing unit converts the voltage output to a pressure value representing the air pressure data transmitted to the display device.

2. The respiratory device of claim 1, wherein the connector comprises a first valve and a second valve arranged to close the second flow path when air moves along the first flow path, and to close the first flow path when air moves along the second flow path.

3. The respiratory device of claim 1, wherein the air pressure data is chosen from the group consisting of an inhale pressure, an exhale pressure, a date, and a time.

4. The respiratory device of claim 1, wherein the display device the processing unit is configured to connect to is chosen from the group consisting of a smartphone, a tablet, a personal computer, a laptop or a mobile device.

5. The respiratory device of claim 1, wherein the inspiratory training tube and the expiratory training tube are detachable from the connector.

6. The respiratory device of claim 5, further comprising an attachment for measuring a maximum exhale pressure when the user exhales through the mouthpiece and a maximum inhale pressure when the user inhales through the mouthpiece.

7. The respiratory device of claim 6, wherein a user inputs a training value into the processing unit prior to measuring the maximum exhale pressure and the maximum inhale pressure.

8. The respiratory device of claim 7, wherein a user inputs a training session duration into the processing unit prior to beginning the training session.

9. The respiratory device of claim 7, wherein the processing unit is configured to transmit live air pressure data and the results of the training session in a format that is displayed from the display device both visually and audibly.

10. The respiratory device of claim 1, wherein the processing unit is configured to receive user input, to display prompts guiding a user through a training session with the respiratory device, and to display live air pressure data during the training session.

11. The respiratory device of claim 1, wherein each of the first actuator and the second actuator changes the compression of a spring connected to one of the inspiratory valve or the expiratory valve, thereby changing a force applied to one of the inspiratory valve or the expiratory valve by said spring.

12. The respiratory device of claim 11, further comprising at least one screw that turns in response to manual rotation, thereby causing the first actuator or second actuator to change the compression of said spring and said force applied to one of the inspiratory valve or the expiratory valve by said spring.

13. The respiratory device of claim 1, wherein the processing unit is configured to send electronic commands to at least one of the first actuator and second actuator that adjust at least one of the first actuator and the second actuator in response to user input.

14. The respiratory device of claim 1, further comprising a bi-directional valve to close the second flow path when air moves along the first flow path, and to close the first flow path when air moves along the second flow path.

* * * * *